US012735773B2

(12) United States Patent
Roth

(10) Patent No.: US 12,735,773 B2
(45) Date of Patent: Sep. 15, 2026

(54) METAL ALLOY HAVING RHENIUM EFFECT

(71) Applicant: Mirus LLC, Marietta, GA (US)

(72) Inventor: Noah Roth, Marietta, GA (US)

(73) Assignee: MiRus LLC, Marietta, GA (US)

( * ) Notice: Subject to any disclaimer, the term of this patent is extended or adjusted under 35 U.S.C. 154(b) by 303 days.

(21) Appl. No.: 18/228,456

(22) Filed: Jul. 31, 2023

(65) Prior Publication Data

US 2024/0150872 A1 May 9, 2024

Related U.S. Application Data

(60) Provisional application No. 63/422,619, filed on Nov. 4, 2022.

(51) Int. Cl.

*C22C 27/00* (2006.01)
*A61L 27/04* (2006.01)
*A61L 27/54* (2006.01)
*B22F 1/065* (2022.01)
*B22F 10/22* (2021.01)

(52) U.S. Cl.

CPC ............ *C22C 27/00* (2013.01); *A61L 27/047* (2013.01); *A61L 27/54* (2013.01); *B22F 1/065* (2022.01); *B22F 10/22* (2021.01); *B22F 2301/20* (2013.01)

(58) Field of Classification Search

CPC ......... C22C 38/00; C22C 38/18; C22C 38/40; C22C 27/00; C22C 33/0285; A61L 27/047

See application file for complete search history.

(56) References Cited

U.S. PATENT DOCUMENTS 5,939,204 A * 8/1999 Czech ..................... C22C 38/18 420/443
11,266,767 B2 3/2022 Roth et al.
2002/0197502 A1 12/2002 Zhao et al.
2005/0079200 A1 4/2005 Rathenow et al.
2006/0200224 A1 9/2006 Furst et al.
2008/0166255 A1 7/2008 Yang et al.
2008/0166596 A1 7/2008 Das et al.
2009/0068249 A1 3/2009 Furst et al.
2010/0023115 A1 1/2010 Robain et al.
2013/0216421 A1 8/2013 Buckman, Jr. et al.
2014/0099279 A1 4/2014 Furst et al.
2016/0237541 A1 8/2016 Patel et al.
2017/0216494 A1 8/2017 Roth et al.
2017/0273785 A1 9/2017 Seguin et al.
2018/0361017 A1 12/2018 Roth
2019/0046684 A1 2/2019 Roth et al.
2020/0306067 A1 10/2020 Nia

FOREIGN PATENT DOCUMENTS

EP 1467003 A1 10/2004
WO 2005024080 A1 3/2005
WO 2006096230 A2 9/2006
WO WO-2009079282 A1 * 6/2009 .............. B22F 5/009

OTHER PUBLICATIONS

Pedowitz et al., "Molybdenum Rhenium (MoRe) as a Biologically superior Alloy for Foot and Ankle Implants" Foot & Ankle Orthopaedics, vol. 3, p. 1 (Sep. 2018).
Badcock, Gordon; Supplementary European Search Report and Opinion of the International Searching Authority issued in International Application No. PCT/US2023014371; dated Dec. 16, 2025; 13 pages.

* cited by examiner

*Primary Examiner* — Jessee R Roe

(74) *Attorney, Agent, or Firm* — UB Greensfelder LLP; Brian E. Turung

(57) ABSTRACT

A medical device that is at least partially formed of a metal alloy that includes at least 15 awt. % rhenium, and a medical device that is partially or fully formed of such metal alloy.

12 Claims, 3 Drawing Sheets

METAL ALLOY HAVING RHENIUM EFFECT

The present application claims priority on U.S. Provisional Application Ser. No. 63/422,619 filed Nov. 4, 2022, which is incorporated herein by reference.

The disclosure relates rhenium containing metal alloys, particularly to metal alloys that have a sufficient quantity of rhenium such that the ductility and tensile strength of the metal alloy is improved, and more particularly to metal alloys that have a sufficient quantity of rhenium such that the ductility and tensile strength of the metal alloy is improved and which such rhenium containing metal alloys can be used to partially or fully form a medical device.

BACKGROUND OF DISCLOSURE

Standard stainless steel, standard cobalt-chromium alloys, and standard TiAlV alloys are some of the more common metal alloys used for medical devices. Although these alloys have been successful in forming a variety of medical devices, these alloys have several deficiencies.

Many cardiovascular devices such as stents, expandable heart valves, and the like are inserted into a patient via the vascular system of a patient and then expanded at the treatment site. These devices are typically crimped onto a catheter prior to insertion into a patient. The minimum diameter to which the cardiovascular device can be crimped onto the catheter will set a limit to the size of the cardiovascular passageway (e.g., blood vessel) to which the cardiovascular device can be inserted. Smaller crimp diameters can result in reduced damage to a blood vessel and/or organ (e.g., heart, etc.) when inserting into and/or placing the cardiovascular device at the treatment site. Smaller crimp diameters can also allow the cardiovascular device to be placed in smaller diameter blood vessels (e.g., blood vessels located in the brain, etc.).

The crimp diameter of the expandable cardiovascular device can be reduced by reducing the thickness and/or size of the frame, struts, etc., of the cardiovascular device. However, such reduction in size also affects the strength of the cardiovascular device after being expanded. After the cardiovascular device is expanded, it must retain its expanded shape at the treatment area, otherwise the cardiovascular device could become dislodged from the treatment area, could damage the treatment area, and/or fail to properly function at the treatment area. As such, cardiovascular devices formed of tradition materials such as standard stainless steel (e.g., 316L: 17-19 wt. % chromium, 13-15 wt. % nickel, 2-4 wt. % molybdenum, 2 wt. % max manganese, 0.75 wt. % max silicon, 0.03 wt. % max carbon, balance iron) and standard cobalt-chromium alloys (e.g., MP35N: 19-21 wt. % chromium, 34-36 wt. % nickel, 9-11 wt. % molybdenum, 1 wt. % max iron, 1 wt. % max titanium, 0.15 wt. % max manganese, 0.15 wt. % max silver, 0.025 wt. % max carbon, balance cobalt) are required to maintain a frame and/or strut size/thickness that limits how small of crimping diameter can be obtained by the crimped cardiovascular device. Other types of standard cobalt-chromium alloys that have been used are standard Phynox and standard Elgiloy alloy (38-42 wt. % cobalt, 18-22 wt. % chromium, 14-18 wt. % iron, 13-17 wt. % nickel, 6-8 wt. % molybdenum), and L605 alloy (18-22 wt. % chromium, 14-16 wt. % W, 9-11 wt. % nickel, balance cobalt). Standard TiAlV alloys are also used in many medical devices (e.g., Ti-6Al-4V; 5.5-6.5 wt. % aluminum, 3.5-4.5 wt. % vanadium and balance titanium; 3.5-4.5 wt. % vanadium, 5.5-6.75 wt. % aluminum, 0.3 wt. % max iron, 0.2 wt. % max oxygen, 0.08 wt. % max carbon, 0.05 wt. % max nitrogen, 0.015 wt. % max hydrogen, 0.05 wt. % max yttrium, balance titanium).

Also, traditional materials such as standard stainless steel (316L) and standard cobalt-chromium alloys (e.g., MP35N, etc.) have a degree of recoil after being crimped and expanded that can interfere with obtaining a minimum crimping diameter and/or can adversely affect the placement of the expandable cardiovascular device at a treatment area. During a crimping process, a crimping device is typically used to crimp the cardiovascular device onto a catheter. After an initial crimping process, tradition materials such as stainless steel and cobalt-chromium alloys recoil to a larger diameter by 9+% of the minimum crimped diameter. As such, the cardiovascular device must be crimped multiple times onto a catheter to attempt to obtain a smaller crimped diameter on the catheter. However, subjecting the cardiovascular device to multiple crimpings can result in damage to the cardiovascular device (e.g., damage to the frame and/or struts of the cardiovascular device, damage to leaflets on an expandable heart valve, etc.). Likewise, when the cardiovascular device is expanded at a treatment area, the traditional materials of the cardiovascular device will recoil 9+% of the maximum expanded diameter. As such, the inflatable balloon on the catheter must be pressurized multiple times to repeatedly expand the cardiovascular device at the treatment area to ensure proper expansion of the cardiovascular device. However, subjecting the cardiovascular device to multiple balloon expansions can result in damage to the cardiovascular device (e.g., damage or breakage of a frame and/or strut, etc.) and/or damage to the treatment area (e.g., rupture of blood vessel, tear and/or puncture of tissue of an organ, etc.).

In view of the current state of the art of medical devices, there is a need for an improved medical device that a) produces less recoil compared to medical devices formed of standard stainless steel, standard cobalt-chromium alloys, or standard TiAlV alloys, and b) can form smaller crimping diameters compared to medical devices formed of standard stainless steel, standard cobalt-chromium alloys, or standard TiAlV alloys.

SUMMARY OF THE DISCLOSURE

The present disclosure is direct to rhenium containing metal alloys, particularly to metal alloys that have a sufficient quantity of rhenium such that the ductility and tensile strength of the metal alloy is improved, and more particularly to metal alloys that have a sufficient quantity of rhenium such that the ductility and tensile strength of the metal alloy is improved and which such rhenium containing metal alloys can be used to partially or fully form a medical device.

In one non-limiting aspect of the present disclosure, there is provided a medical device that is at least partially made of a rhenium containing metal alloy. The medical device can include an orthopedic device, PFO (patent foramen ovale) device, stent, valve (e.g., heart valve, TAVR valve, mitral valve replacement, tricuspid valve replacement, pulmonary valve replacement, etc.), spinal implant, frame and other structures for use with a spinal implant, vascular implant, graft, guide wire, sheath, catheter, needle, stent catheter, electrophysiology catheter, hypotube, staple, cutting device, any type of implant, pacemaker, dental implant, dental crown, dental braces, wire used in medical procedures, bone implant, artificial disk, artificial spinal disk, prosthetic implant or device to repair, replace and/or support a bone (e.g., acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, zygomatic bone, etc.) and/or cartilage, bone plate nail, rod, screw, post, cage, plate, pedicle screw, cap, hinge, joint system, anchor, spacer, shaft, anchor, disk, ball, tension band, locking connector other structural assembly that is used in a body to support a structure, mount a structure, and/or repair a structure in a body such as, but not limited to, a human body, animal body, etc. In one non-limiting embodiment, the medical device includes an expandable frame (e.g., stent, prosthetic heart valve, etc.) that can plastically deform radially outwardly by an expansion arrangement (e.g., inflatable balloon, etc.). In another non-limiting embodiment, the metal alloy is not a self-expanding alloy. In another non-limiting embodiment, the medical device that is formed of 10-100% (and all values and ranges therebetween) of a metal alloy that includes rhenium in a sufficient amount to create a “rhenium effect” in the metal alloy. In another non-limiting embodiment, the medical device that is formed of 50-100% of a metal alloy that includes rhenium in a sufficient amount to create a “rhenium effect” in the metal alloy.

In accordance with another and/or alternative aspect of the present disclosure, there is provided a metal alloy that includes rhenium in a sufficient quantity as to create a “rhenium effect” in the metal alloy. As defined herein, a “rhenium effect” is a) an increase of at least 10% in ductility of the metal alloy caused by the addition of rhenium to the metal alloy, and/or b) an increase of at least 10% in tensile strength of the metal alloy caused by the addition of rhenium to the metal alloy. It has been found for many metal alloys (e.g., standard stainless steel, standard CoCr alloys, standard TiAlV alloys, standard aluminum alloys, standard nickel alloys, standard titanium alloys, standard tungsten alloys, standard molybdenum alloys, standard copper alloys, standard MP35N alloys, standard beryllium-copper alloys, etc.) results in improved ductility and/or tensile strength. It has been found that the addition of rhenium to a metal alloy can result in the formation of a twining alloy in the metal alloy that results in the overall ductility of the metal alloy to increase as the yield and tensile strength increases as a result of reduction and/or work hardening of the metal alloy that includes the rhenium addition. The rhenium effect occurs when the atomic weight of rhenium in the metal alloy is at least 15% (e.g., 15-99 awt. % rhenium in the metal alloy and all values and ranges therebetween). For example, for standard stainless steel alloys, the rhenium effect can begin to be present when the stainless steel alloy is modified to include a rhenium amount of at least 5-10 wt. % (and all values and ranges therebetween) of the stainless steel alloy. For standard CoCr alloys, the rhenium effect can begin to be present when the CoCr alloy is modified to include a rhenium amount of at least 4.8-9.5 wt. % (and all values and ranges therebetween) of the CoCr alloy. For standard TiAlV alloys, the rhenium effect can begin to be present when the TiAlV alloy is modified to include a rhenium amount of at least 4.5-9 wt. % (and all values and ranges therebetween) of the TiAlV alloy. At can be appreciated, the rhenium content in the above examples can be greater than the minimum amount to create the rhenium effect in the metal alloy.

In accordance with another and/or alternative aspect of the present disclosure, the metal alloy includes at least 15 awt. % rhenium, and at least 0.1 wt. % (e.g., 0.1 wt. % to 96 wt. % and all values and ranges therebetween) of one or more metals aluminum, bismuth, chromium, cobalt, copper, hafnium, iridium, iron, magnesium, manganese, molybdenum, nickel, niobium, osmium, rhodium, ruthenium, silicon, silver, tantalum, technetium, titanium, tungsten, vanadium, yttrium, zirconium.

In accordance with another and/or alternative aspect of the present disclosure, the metal alloy includes rhenium in a sufficient amount to create a rhenium effect in the metal alloy, and the metal alloy is a refractory metal alloy. As defined herein, a refractory metal alloy is a metal alloy that includes at least 20 wt. % of one or more of molybdenum, rhenium, niobium, tantalum or tungsten. Non-limiting metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc.

In accordance with another and/or alternative aspect of the present disclosure, the metal alloy that includes rhenium in a sufficient amount to create a rhenium effect in the metal alloy, and the metal alloy is a standard stainless steel alloy that has been modified to include at least 15 awt. % rhenium. As defined herein, a standard stainless steel alloy includes 10-28 wt. % chromium, 0-35 wt. % nickel, 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, 0-2 wt. % tungsten, and at least 50 wt. % iron. A standard 316L alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron.

In accordance with another and/or alternative aspect of the present disclosure, the metal alloy that includes rhenium in a sufficient amount to create a rhenium effect in the metal alloy, and the metal alloy is a standard cobalt chromium alloy that has been modified to include at least 15 awt. % rhenium. As defined herein, a standard CoCr alloy includes 15-32 wt. % chromium, 1-36% wt. % nickel, 2-18 wt. % molybdenum, 0-18 wt. % iron, 0-1 wt. % titanium, 0-0.15 wt. % manganese, 0-0.15 wt. % silver, 0-0.025 wt. % carbon, 0-16 wt. % tungsten, 0-2 wt. % Si, 0-2 wt. % aluminum, 0-1 wt. % iron, 30-68 wt. % cobalt. A standard MP35N alloy includes 19-21 wt. % chromium, 34-36 wt. % nickel, 9-11 wt. % molybdenum, 1 wt. % max iron, 1 wt. % max titanium, 0.15 wt. % max manganese, 0.15 wt. % max silver, 0.025 wt. % max carbon, balance cobalt. A standard Phynox and standard Elgiloy alloy includes 38-42 wt. % cobalt, 18-22 wt. % chromium, 14-18 wt. % iron, 13-17 wt. % nickel, 6-8 wt. % molybdenum. A standard L605 alloy includes 18-22 wt. % chromium, 14-16 wt. % tungsten, 9-11 wt. % nickel, balance cobalt.

In accordance with another and/or alternative aspect of the present disclosure, the metal alloy that includes rhenium in a sufficient amount to create a rhenium effect in the metal alloy, and the metal alloy is a standard TiAlV alloy that has been modified to include at least 15 awt. % rhenium. A standard TiAlV alloy includes 5.5-6.75 wt. % aluminum, 3.5-4.5 wt. % vanadium, 85-93 wt. % titanium, 0-0.4 wt. % iron, 0-0.2 wt. % carbon. A standard Ti-6Al-4V alloy incudes 3.5-4.5 wt. % vanadium, 5.5-6.75 wt. % aluminum, 0.3 wt. % max iron, 0.2 wt. % max oxygen, 0.08 wt. % max carbon, 0.05 wt. % max nitrogen, 0.015 wt. % max hydrogen H, 0.05 wt. % max yttrium, balance titanium.

In accordance with another and/or alternative aspect of the present disclosure, the metal alloy that includes rhenium in a sufficient amount to create a rhenium effect in the metal alloy, and the metal alloy is a standard aluminum alloy that has been modified to include at least 15 awt. % rhenium. As defined herein, a standard aluminum alloy includes 80-99 wt. % aluminum, 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper.

In accordance with another and/or alternative aspect of the present disclosure, the metal alloy that includes rhenium in a sufficient amount to create a rhenium effect in the metal alloy, and the metal alloy is a standard nickel alloy that has been modified to include at least 15 awt. % rhenium. As defined herein, standard nickel alloy includes 30-98 wt. % nickel, 5-25 wt. % chromium, 0-65 wt. % iron, 0-30 wt. % molybdenum, 0-32% wt. % copper, 0-32% wt. % cobalt, 2-2 wt. % aluminum, 0-6 wt. % tantalum, 0-15% wt. % tungsten, 0-5 wt. % titanium, 0-6 wt. % niobium, 0-3 wt. % silicon.

In accordance with another and/or alternative aspect of the present disclosure, the metal alloy that includes rhenium in a sufficient amount to create a rhenium effect in the metal alloy, and the metal alloy is a standard titanium alloy that has been modified to include at least 15 awt. % rhenium. As defined herein, standard titanium alloy includes 80-99 wt. % titanium, 0-6 wt. % aluminum, 0-3 wt. % tin, 0-1 wt. % palladium, 0-8 wt. % vanadium, 0-15% wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron.

In accordance with another and/or alternative aspect of the present disclosure, the metal alloy that includes rhenium in a sufficient amount to create a rhenium effect in the metal alloy, and the metal alloy is a standard tungsten alloy that has been modified to include at least 15 awt. % rhenium. As defined herein, standard tungsten alloy includes 85-98 wt. % tungsten, 0-8 wt. % nickel, 0-5 wt. % copper, 0-5 wt. % molybdenum, 0-4 wt. % iron.

In accordance with another and/or alternative aspect of the present disclosure, the metal alloy that includes rhenium in a sufficient amount to create a rhenium effect in the metal alloy, and the metal alloy is a standard molybdenum alloy that has been modified to include at least 15 awt. % rhenium. As defined herein, standard molybdenum alloy includes 90-99.5 wt. % molybdenum, 0-1 wt. % nickel, 0-1 wt. % titanium, 0-1 wt. % zirconium, 0-30 wt. % tungsten, 0-2 wt. % hafnium, 0-2 wt. % lanthanum.

In accordance with another and/or alternative aspect of the present disclosure, the metal alloy that includes rhenium in a sufficient amount to create a rhenium effect in the metal alloy, and the metal alloy is a standard copper alloy that has been modified to include at least 15 awt. % rhenium. As defined herein, a standard copper alloy includes 55-95 wt. % copper, 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 Wt. % cobalt, 0-20% wt. % nickel.

In accordance with another and/or alternative aspect of the present disclosure, the metal alloy that includes rhenium in a sufficient amount to create a rhenium effect in the metal alloy, and the metal alloy is a standard MP35N alloy that has been modified to include at least 15 awt. % rhenium. As defined herein, a standard MP35N alloy includes 32-38 wt. % nickel, 18-22 wt. % chromium, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. % phosphorous, 0-0.1 wt. % boron, 0-0.1 wt. % sulfur, and the balance cobalt.

In accordance with another and/or alternative aspect of the present disclosure, the metal alloy that includes rhenium in a sufficient amount to create a rhenium effect in the metal alloy, and the metal alloy is a standard beryllium-copper alloy that has been modified to include at least 15 awt. % rhenium. As defined herein, a standard beryllium-copper alloy includes 95-98.5 wt. % copper, 1-4 wt. % beryllium, 0-1 wt. % cobalt, and 0-0.5 wt. % silicon.

Several non-limiting examples of metal alloys that can be used to partially or fully form the frame of the medical device are set forth below in weight percent.

| Component/Wt. % | Ex. 1 | Ex. 2 | Ex. 3 | Ex. 4 |
|---|---|---|---|---|
| Ag | 0-40% | 0-40% | 0-40% | 0-40% |
| Al | 0-95% | 0-95% | 0-40% | 0-40% |
| B | 0-3% | 0-2% | 0-1% | 0-1% |
| Be | 0-10% | 0-8% | 0-5% | 0-5% |
| Bi | 0-40% | 0-40% | 0-40% | 0-40% |
| Ca | 0-5% | 0-4% | 0-2% | 0-2% |
| Cd | 0-4% | 0-3% | 0-3% | 0-2% |
| Ce | 0-8% | 0-5% | 0-3% | 0-3% |
| Cr | 0-40% | 0-40% | 0-40% | 0-40% |
| Cu | 0-95% | 0-80% | 0-40% | 0-40% |
| Co | 0-70% | 0-70% | 0-70% | 0-60% |
| Fe | 0-90% | 0-80% | 0-80% | 0-80% |
| Ga | 0-3% | 0-2% | 0-1% | 0-1% |
| Hf | 0-40% | 0-40% | 0-40% | 0-40% |
| Ir | 0-40% | 0-40% | 0-40% | 0-40% |
| La | 0-5% | 0-5% | 0-4% | 0-3% |
| Li | 0-8% | 0-6% | 0-4% | 0-3% |
| Mg | 0-40% | 0-40% | 0-40% | 0-40% |
| Mn | 0-40% | 0-40% | 0-40% | 0-40% |
| Mo | 0-90% | 10-90% | 20-85% | 40-80% |
| Nb | 0-80% | 0-80% | 0-80% | 0-80% |
| Ni | 0-90% | 0-90% | 0-60% | 0-60% |
| Os | 0-40% | 0-40% | 0-40% | 0-40% |
| Pb | 0-5% | 0-4% | 0-45 | 0-2% |
| Pd | 0-4% | 0-3% | 0-2% | 0-2% |
| Pt | 0-40% | 0-40% | 0-40% | 0-40% |
| Re | 0-98% | 10-90% | 20-80% | 30-70% |

-continued

| | | | | |
|---|---|---|---|---|
| Rh | 0-40% | 0-40% | 0-40% | 0-40% |
| Ru | 0-4% | 0-2% | 0-2% | 0-1% |
| Sc | 0-8% | 0-5% | 0-4% | 0-4% |
| Si | 0-40% | 0-40% | 0-40% | 0-40% |
| Sn | 0-40% | 0-40% | 0-40% | 0-40% |
| Ta | 0-80% | 0-60% | 0-80% | 0-80% |
| Tc | 0-40% | 0-40% | 0-40% | 0-40% |
| Ti | 0-90% | 0-80% | 0-60% | 0-60% |
| V | 0-40% | 0-40% | 0-40% | 0-40% |
| W | 0-94% | 0-94% | 0-90% | 0-90% |
| Y | 0-40% | 0-40% | 0-40% | 0-40% |
| Zr | 0-40% | 0-40% | 0-40% | 0-40% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.4% | <0.3% | <0.06% | <0.06% |
| N | <0.06% | <0.06% | <0.06% | <0.06% |
| O | <0.06% | <0.06% | <0.06% | <0.06% |
| P | <0.2% | <0.1% | <0.05% | <0.05% |
| S | <0.2% | <0.1% | <0.05% | <0.05% |
| H | <0.2% | <0.1% | <0.05% | <0.05% |

| Component/Wt. % | Ex. 5 | Ex. 6 | Ex. 7 | Ex. 8 |
|---|---|---|---|---|
| Ag | 0-20% | 0-20% | 0-20% | 0-20% |
| Al | 0-35% | 0-30% | 5-30% | 0-25% |
| Bi | 0-20% | 0-20% | 0-20% | 0-20% |
| Cr | 10-40% | 0-40% | 0-40% | 0-40% |
| Cu | 0-20% | 0-20% | 0-20% | 0-20% |
| Co | 10-60% | 0-60% | 0-60% | 0-60% |
| Fe | 0-80% | 30-80% | 0-80% | 0-70% |
| Hf | 0-20% | 0-20% | 0-20% | 0-20% |
| Ir | 0-20% | 0-20% | 0-20% | 0-20% |
| Mg | 0-20% | 0-20% | 0-20% | 0-20% |
| Mn | 0-20% | 0-40% | 0-20% | 0-20% |
| Mo | 0-60% | 0-60% | 0-80% | 0-70% |
| Nb | 0-60% | 0-60% | 0-65% | 20-60% |
| Ni | 0-60% | 5-55% | 0-52% | 0-50% |
| Os | 0-20% | 0-20% | 0-20% | 0-20% |
| Pt | 0-20% | 0-20% | 0-20% | 0-20% |
| Re | 4.5-98% | 4.5-90% | 4.5-80% | 4.5-70% |
| Rh | 0-20% | 0-20% | 0-20% | 0-20% |
| Si | 0-20% | 0-20% | 0-20% | 0-20% |
| Sn | 0-20% | 0-20% | 0-20% | 0-20% |
| Ta | 0-60% | 0-60% | 5-65% | 0-60% |
| Tc | 0-20% | 0-20% | 0-20% | 0-20% |
| Ti | 0-60% | 0-55% | 0-53% | 0-50% |
| V | 0-20% | 0-20% | 2-20% | 0-20% |
| W | 0-60% | 0-60% | 0-80% | 0-70% |
| Y | 0-20% | 0-20% | 0-20% | 0-20% |
| Zr | 0-20% | 0-20% | 0-20% | 5-20% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 9 | Ex. 10 | Ex. 11 | Ex. 12 |
|---|---|---|---|---|
| Ag | 0-5% | 0-5% | 0-5% | 0-5% |
| Al | 0-5% | 0-5% | 1-15% | 0-20% |
| Bi | 0-5% | 0-5% | 0-5% | 0-5% |
| Cr | 1-28% | 1-30% | 0-5% | 0-30% |
| Cu | 0-20% | 0-5% | 0-5% | 0-25% |
| Co | 0-5% | 1-60% | 0-5% | 0-60% |
| Fe | 10-80% | 0-25% | 0-5% | 0-80% |
| Hf | 0-5% | 0-5% | 0-5% | 0-5% |
| Ir | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-8% | 0-25% | 0-5% | 0-98% |
| Nb | 0-5% | 0-5% | 0-5% | 0-95% |
| Ni | 1-20% | 1-45% | 0-5% | 0-50% |
| Os | 0-5% | 0-5% | 0-5% | 0-5% |
| Pt | 0-5% | 0-5% | 0-5% | 0-5% |
| Re | 5-20% | 4.8-20% | 4.5-20% | 4.5-20% |

-continued

| | | | | |
|---|---|---|---|---|
| Rh | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-98% |
| Tc | 0-5% | 0-5% | 0-5% | 0-5% |
| Ti | 0-5% | 0-5% | 40-93% | 0-93% |
| V | 0-5% | 0-5% | 1-10% | 0-20% |
| W | 0-5% | 0-20% | 0-5% | 0-98% |
| Y | 0-5% | 0-5% | 0-5% | 0-5% |
| Zr | 0-5% | 0-5% | 0-5% | 0-5% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 13 | Ex. 14 | Ex. 15 | Ex. 16 |
|---|---|---|---|---|
| Mo | 40-80% | 40-80% | 40-80% | 40-80% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | ≤1% | ≤1% | ≤1% |
| $La_2O_3$ | 0-32% | 0.1-2% | 0-2% | 0-2% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 7-49% | 7.5-49% | 7.5-49% | 7.5-49% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| CNT | 0-10% | 0-10% | 0-10% | 0-10% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 17 | Ex. 18 | Ex. 19 |
|---|---|---|---|
| Mo | 40-80% | 40-80% | 40-80% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 7-49% | 7.5-49% | 7.5-49% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| CNT | 0-10% | 0-10% | 0-10% |
| C | <0.06% | <0.06% | <0.06% |
| N | <0.06% | <0.06% | <0.06% |
| O | <0.06% | <0.06% | <0.06% |

-continued

| Component/Wt. % | Ex. 20 | Ex. 21 | Ex. 22 |
|---|---|---|---|
| Mo | 45-78% | 45-75% | 45-70% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 7-49% | 7.5-49% | 7.5-49% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| CNT | 0-10% | 0-10% | 0-10% |
| C | <0.06% | <0.06% | <0.06% |
| N | <0.06% | <0.06% | <0.06% |
| O | <0.06% | <0.06% | <0.06% |

| Component/Wt. % | Ex. 23 | Ex. 24 | Ex. 25 | Ex. 26 |
|---|---|---|---|---|
| Mo | 35-80% | 35-80% | 35-70% | 35-65% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2% | 0-2.5% | 0-2.5% |
| $La_2O_3$ | 0-2% | 0.3-0.7% | 0-2% | 0-2% |
| Re | 7-49% | 7-49% | 7.5-49% | 7.5-49% |
| Ta | 0-2% | 0-2% | 0-50% | 0-50% |
| W | 0-2% | 0-2% | 0-50% | 20-50% |
| $Y_2O_3$ | 0-1% | 0-1% | 0.3-0.5% | 0-1% |
| $ZrO_2$ | 0-3% | 0-3% | 0-3% | 0-3% |

| Component/Wt. % | Ex. 27 | Ex. 28 | Ex. 29 |
|---|---|---|---|
| Mo | 40-60% | 35-60% | 30-60% |
| C | 0-0.15% | 0-0.15% | 0-0.15% |
| $Cs_2O$ | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 7-60% | 7.5-65% | 7.5-70% |
| Ta | 0-3% | 10-50% | 0-40% |
| W | 0-3% | 0-50% | 0-40% |
| $Y_2O_3$ | 0-1% | 0-1% | 0-1% |
| $ZrO_2$ | 1.2-1.8% | 0-3% | 0-3% |

| Component/Wt. % | Ex. 30 | Ex. 31 | Ex. 32 |
|---|---|---|---|
| W | 20-80% | 60-80% | 20-78% |
| Re | 7.5-47.5% | 10-40% | 8-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |

-continued

| | | | |
|---|---|---|---|
| $Y_2O_3$ | <0.5% | <0.5% | <0.5% |
| Zr | <0.5% | <0.5% | <0.5% |
| $ZrO_2$ | <0.5% | <0.5% | <0.5% |
| CNT | 0-10% | 0-10% | <0.5%. |
| C | <0.06% | <0.06% | <0.06% |
| N | <0.06% | <0.06% | <0.06% |
| O | <0.06% | <0.06% | <0.06% |

| Component/Wt. % | Ex. 33 | Ex. 34 | Ex. 35 |
|---|---|---|---|
| W | 20-80% | 60-80% | 20-75% |
| Re | 7.5-47.5% | 10-40% | 7.5-47.5% |
| Mo | 0-47.5% | <0.5% | 1-47.5% |

| Component/Wt. % | Ex. 36 | Ex. 37 | Ex. 38 |
|---|---|---|---|
| W | 50.1-80% | 65-80% | 50.1-79% |
| Re | 10-40% | 10-35% | 10-40% |
| Mo | 0-40% | <0.5% | 1-30% |

| Component/Wt. % | Ex. 39 | Ex. 40 | Ex. 41 |
|---|---|---|---|
| W | 20-49% | 20-49% | 20-49% |
| Re | 7.5-60% | 7.5-60% | 7.5-60% |
| Mo | 0-40% | 0-40% | 0-39% |

| Component/Wt. % | Ex. 42 | Ex. 43 | Ex. 44 |
|---|---|---|---|
| Re | 5-98% | 60-95% | 80-90% |
| Mo | 0-80% | 0-40% | 0-20% |
| W | 0-80% | 0-40% | 0-20% |

| Component/Wt. % | Ex. 45 | Ex. 46 | Ex. 47 |
|---|---|---|---|
| W | 20-49% | 20-49% | 20-49% |
| Re | 6-40% | 6-40% | 6-39% |
| Mo | 20-60% | 30-60% | 40-60% |

| Component/Wt. % | Ex. 48 | Ex. 49 | Ex. 50 |
|---|---|---|---|
| W | 20-40% | 20-35% | 20-30% |
| Re | 6-40% | 6-40% | 6-40% |
| Mo | 0-40% | 10-40% | 31-40% |

| Component/Wt. % | Ex. 51 | Ex. 52 | Ex. 53 | Ex. 54 |
|---|---|---|---|---|
| Re | 5-60% | 5-60% | 5-60% | 5-60% |
| Mo | 0-55% | 10-55% | 10-55% | 10-55% |
| Bi | 1-42% | 0-32% | 0-32% | 0-32% |
| Cr | 0-32% | 1-42% | 0-32% | 0-32% |
| Ir | 0-32% | 0-32% | 1-42% | 0-32% |
| Nb | 0-32% | 0-32% | 0-32% | 1-42% |
| Ta | 0-32% | 0-32% | 0-32% | 0-32% |
| Ti | 0-32% | 0-32% | 0-32% | 0-32% |
| Y | 0-32% | 0-32% | 0-32% | 0-32% |
| Zr | 0-32% | 0-32% | 0-32% | 0-32% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 55 | Ex. 56 | Ex. 57 | Ex. 58 |
|---|---|---|---|---|
| Re | 5-60% | 5-60% | 5-60% | 5-60% |
| Mo | 15-55% | 15-55% | 15-55% | 15-55% |
| Bi | 0-32% | 0-32% | 0-32% | 0-32% |
| Cr | 0-32% | 0-32% | 0-32% | 0-32% |
| Ir | 0-32% | 0-32% | 0-32% | 0-32% |
| Nb | 0-32% | 0-32% | 0-32% | 0-32% |
| Ta | 1-42% | 0-32% | 0-32% | 0-32% |
| Ti | 0-32% | 1-42% | 0-32% | 0-32% |
| Y | 0-32% | 0-32% | 1-42% | 0-32% |
| Zr | 0-32% | 0-32% | 0-32% | 1-42% |
| C | <0.06% | <0.06% | <0.06% | <0.06% |
| N | <0.06% | <0.06% | <0.06% | <0.06% |
| O | <0.06% | <0.06% | <0.06% | <0.06% |

-continued

| Component/Wt. % | Ex. 59 | Ex. 60 | Ex. 61 | Ex. 62 |
| --- | --- | --- | --- | --- |
| Re | 41-59% | 41-59% | 41-59% | 41-59% |
| Mo | 18-45% | 18-45% | 18-45% | 18-45% |
| Bi | 1-42% | 0-32% | 0-32% | 0-32% |
| Cr | 0-32% | 1-42% | 0-32% | 0-32% |
| Ir | 0-32% | 0-32% | 1-42% | 0-32% |
| Nb | 0-32% | 0-32% | 0-32% | 1-42% |
| Ta | 0-32% | 0-32% | 0-32% | 0-32% |
| Ti | 0-32% | 0-32% | 0-32% | 0-32% |
| Y | 0-32% | 0-32% | 0-32% | 0-32% |
| Zr | 0-32% | 0-32% | 0-32% | 0-32% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 63 | Ex. 64 | Ex. 65 | Ex. 66 |
| --- | --- | --- | --- | --- |
| Re | 41-59% | 41-59% | 41-59% | 41-59% |
| Mo | 18-45% | 18-45% | 18-45% | 18-45% |
| Bi | 0-32% | 0-32% | 0-32% | 0-32% |
| Cr | 0-32% | 0-32% | 0-32% | 0-32% |
| Ir | 0-32% | 0-32% | 0-32% | 0-32% |
| Nb | 0-32% | 0-32% | 0-32% | 0-32% |
| Ta | 1-42% | 0-32% | 0-32% | 0-32% |
| Ti | 0-32% | 1-42% | 0-32% | 0-32% |
| Y | 0-32% | 0-32% | 1-42% | 0-32% |
| Zr | 0-32% | 0-32% | 0-32% | 1-42% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 67 | Ex. 68 | Ex. 69 | Ex. 70 |
| --- | --- | --- | --- | --- |
| Re | 41-59% | 41-59% | 41-59% | 41-59% |
| Mo | 18-45% | 18-45% | 18-45% | 18-45% |
| Bi | 0-15% | 0-15% | 1-36% | 0-15% |
| Cr | 1-20% | 1-20% | 1-20% | 1-20% |
| Ir | 0-15% | 0-15% | 0-15% | 0-15% |
| Nb | 1-36% | 0-15% | 0-15% | 0-15% |
| Ta | 0-15% | 1-36% | 0-15% | 0-15% |
| Ti | 0-15% | 0-15% | 0-15% | 0-15% |
| Y | 0-15% | 0-15% | 0-15% | 0-15% |
| Zr | 0-15% | 0-15% | 0-15% | 1-36% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 71 | Ex. 72 | Ex. 73 | Ex. 74 |
| --- | --- | --- | --- | --- |
| Re | 41-59% | 41-59% | 41-59% | 41-59% |
| Mo | 18-45% | 18-45% | 18-45% | 18-45% |
| Bi | 1-36% | 0-15% | 0-15% | 0-15% |
| Cr | 1-20% | 1-20% | 1-20% | 1-20% |
| Ir | 0-15% | 1-36% | 0-15% | 0-15% |
| Nb | 0-15% | 0-15% | 0-15% | 0-15% |
| Ta | 0-15% | 0-15% | 0-15% | 0-15% |
| Ti | 0-15% | 0-15% | 1-36% | 0-15% |
| Y | 0-15% | 0-15% | 0-15% | 1-36% |
| Zr | 0-15% | 0-15% | 0-15% | 0-15% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 75 | Ex. 76 | Ex. 77 | Ex. 78 |
| --- | --- | --- | --- | --- |
| Re | 41-59% | 41-59% | 41-59% | 41-59% |
| Mo | 18-45% | 18-45% | 18-45% | 18-45% |
| Bi | 1-34% | 0-15% | 0-15% | 0-15% |
| Cr | 0-15% | 0-15% | 0-15% | 0-15% |
| Ir | 0-15% | 0-15% | 0-15% | 1-34% |
| Nb | 3-27% | 3-27% | 3-27% | 3-27% |
| Ta | 0-42 | 1-34% | 0-15% | 0-15% |
| Ti | 0-15% | 0-15% | 0-15% | 0-15% |
| Y | 0-15% | 0-15% | 0-15% | 0-15% |
| Zr | 0-15% | 0-15% | 3-27% | 0-15% |
| C | <0.06% | <0.06% | <0.06% | <0.06% |

-continued

| | | | | |
|---|---|---|---|---|
| N | <0.06% | <0.06% | <0.06% | <0.06% |
| O | <0.06% | <0.06% | <0.06% | <0.06% |

| Component/Wt. % | Ex. 79 | Ex. 80 | Ex. 81 | Ex. 82 |
|---|---|---|---|---|
| Re | 41-59% | 41-59% | 41-59% | 41-59% |
| Mo | 18-45% | 18-45% | 18-45% | 18-45% |
| Bi | 0-15% | 0-15% | 0-15% | 0-15% |
| Cr | 0-15% | 0-15% | 0-15% | 0-15% |
| Ir | 0-15% | 1-34% | 0-15% | 0-15% |
| Nb | 0-15% | 0-15% | 0-15% | 0-15% |
| Ta | 1-34% | 0-15% | 3-27% | 0-15% |
| Ti | 0-15% | 0-15% | 0-15% | 0-15% |
| Y | 0-15% | 0-15% | 0-15% | 3-27% |
| Zr | 3-27% | 3-27% | 3-27% | 3-27% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 83 | Ex. 84 | Ex. 85 | Ex. 86 |
|---|---|---|---|---|
| Re | 41-59% | 41-59% | 41-59% | 41-59% |
| Mo | 18-45% | 18-45% | 18-45% | 18-45% |
| Bi | 0-15% | 0-15% | 0-15% | 0-15% |
| Cr | 0-15% | 0-15% | 0-15% | 1-10% |
| Ir | 1-34% | 0-25 | 3-27% | 0-15% |
| Nb | 0-15% | 3-27% | 0-15% | 0-15% |
| Ta | 0-15% | 0-15% | 1-34% | 0-15% |
| Ti | 0-15% | 0-15% | 0-15% | 0-15% |
| Y | 3-27% | 3-27% | 0-15% | 0-15% |
| Zr | 0-15% | 0-15% | 3-27% | 1-12% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 87 | Ex. 88 | Ex. 89 | Ex. 90 |
|---|---|---|---|---|
| Re | 50-75% | 55-75% | 60-75% | 65-75% |
| Cr | 25-50% | 25-45% | 25-40% | 25-35% |
| Mo | 0-25% | 0-25% | 0-25% | 0-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| Ag | 0-25% | 0-25% | 0-25% | 0-25% |
| Al | 0-25% | 0-25% | 0-25% | 0-22% |
| Co | 0-25% | 0-25% | 0-25% | 0-25% |
| Fe | 0-25% | 0-25% | 0-25% | 0-25% |
| Mg | 0-25% | 0-25% | 0-25% | 0-25% |
| Ni | 0-25% | 0-25% | 0-25% | 0-25% |
| Pt | 0-25% | 0-25% | 0-25% | 0-25% |
| Si | 0-25% | 0-25% | 0-25% | 0-25% |
| Sn | 0-25% | 0-25% | 0-25% | 0-25% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 91 | Ex. 92 | Ex. 93 | Ex. 94 |
|---|---|---|---|---|
| Re | 50-72% | 55-72% | 60-72% | 65-72% |
| Cr | 28-50% | 28-45% | 28-40% | 28-35% |

-continued

| | | | | |
|---|---|---|---|---|
| Mo | 0-25% | 0-25% | 0-25% | 0-25% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 95 | Ex. 96 | Ex. 97 | Ex. 98 |
|---|---|---|---|---|
| Re | 50-70% | 55-70% | 60-70% | 65-70% |
| Cr | 30-50% | 30-45% | 30-40% | 30-35% |
| Mo | 0-10% | 0-10% | 0-10% | 0-10% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

-continued

| Component/Wt. % | Ex. 99 | Ex. 100 | Ex. 101 | Ex. 102 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-10% | 0-10% | 0-10% | 0-10% |
| Bi | 0-10% | 0-10% | 0-10% | 0-10% |
| Cr | 0-10% | 0-10% | 0-10% | 0-10% |
| Ir | 0-10% | 0-10% | 0-10% | 0-10% |
| Nb | 0-10% | 0-10% | 0-10% | 0-10% |
| Ta | 0-10% | 0-10% | 0-10% | 0-10% |
| V | 0-10% | 0-10% | 0-10% | 0-10% |
| W | 0-10% | 0-10% | 0-10% | 0-10% |
| Mn | 0-10% | 0-10% | 0-10% | 0-10% |
| Tc | 0-10% | 0-10% | 0-10% | 0-10% |
| Ru | 0-10% | 0-10% | 0-10% | 0-10% |
| Rh | 0-10% | 0-10% | 0-10% | 0-10% |
| Hf | 0-10% | 0-10% | 0-10% | 0-10% |
| Os | 0-10% | 0-10% | 0-10% | 0-10% |
| Cu | 0-10% | 0-10% | 0-10% | 0-10% |
| Ir | 0-10% | 0-10% | 0-10% | 0-10% |
| Ti | 0-10% | 0-10% | 0-10% | 0-10% |
| Y | 0-10% | 0-10% | 0-10% | 0-10% |
| Zr | 0-10% | 0-10% | 0-10% | 0-10% |
| Ag | 0-10% | 0-10% | 0-10% | 0-10% |
| Al | 0-10% | 0-10% | 0-10% | 0-10% |
| Co | 0-10% | 0-10% | 0-10% | 0-10% |
| Fe | 0-10% | 0-10% | 0-10% | 0-10% |
| Mg | 0-10% | 0-10% | 0-10% | 0-10% |
| Ni | 0-10% | 0-10% | 0-10% | 0-10% |
| Pt | 0-10% | 0-10% | 0-10% | 0-10% |
| Si | 0-10% | 0-10% | 0-10% | 0-10% |
| Sn | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 103 | Ex. 104 | Ex. 105 | Ex. 106 |
|---|---|---|---|---|
| Re | 50-67.5% | 55-67.5% | 60-67.5% | 65-67.5% |
| Cr | 32.5-50% | 32.5-45% | 32.5-40% | 32.5-35% |
| Mo | 0-5% | 0-5% | 0-5% | 0-5% |
| Bi | 0-5% | 0-5% | 0-5% | 0-5% |
| Cr | 0-5% | 0-5% | 0-5% | 0-5% |
| Ir | 0-5% | 0-5% | 0-5% | 0-5% |
| Nb | 0-5% | 0-5% | 0-5% | 0-5% |
| Ta | 0-5% | 0-5% | 0-5% | 0-5% |
| V | 0-5% | 0-5% | 0-5% | 0-5% |
| W | 0-5% | 0-5% | 0-5% | 0-5% |
| Mn | 0-5% | 0-5% | 0-5% | 0-5% |
| Tc | 0-5% | 0-5% | 0-5% | 0-5% |
| Ru | 0-5% | 0-5% | 0-5% | 0-5% |
| Rh | 0-5% | 0-5% | 0-5% | 0-5% |
| Hf | 0-5% | 0-5% | 0-5% | 0-5% |
| Os | 0-5% | 0-5% | 0-5% | 0-5% |
| Cu | 0-5% | 0-5% | 0-5% | 0-5% |
| Ir | 0-5% | 0-5% | 0-5% | 0-5% |
| Ti | 0-5% | 0-5% | 0-5% | 0-5% |
| Y | 0-5% | 0-5% | 0-5% | 0-5% |
| Zr | 0-5% | 0-5% | 0-5% | 0-5% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Pt | 0-5% | 0-5% | 0-5% | 0-5% |
| Si | 0-5% | 0-5% | 0-5% | 0-5% |
| Sn | 0-5% | 0-5% | 0-5% | 0-5% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |

-continued

| | | | | |
|---|---|---|---|---|
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 107 | Ex. 108 | Ex. 109 | Ex. 110 |
|---|---|---|---|---|
| Re | 50-75% | 55-72% | 60-70% | 62-70% |
| Cr | 24-49% | 27-44% | 29-39% | 29-37% |
| Mo | 1-15% | 1-10% | 1-8% | 1-5% |
| Bi | 0-15% | 0-10% | 0-8% | 0-5% |
| Ir | 0-15% | 0-10% | 0-8% | 0-5% |
| Nb | 0-15% | 0-10% | 0-8% | 0-5% |
| Ta | 0-15% | 0-10% | 0-8% | 0-5% |
| V | 0-15% | 0-10% | 0-8% | 0-5% |
| W | 0-15% | 0-10% | 0-8% | 0-5% |
| Mn | 0-15% | 0-10% | 0-8% | 0-5% |
| Tc | 0-15% | 0-10% | 0-8% | 0-5% |
| Ru | 0-15% | 0-10% | 0-8% | 0-5% |
| Rh | 0-15% | 0-10% | 0-8% | 0-5% |
| Hf | 0-15% | 0-10% | 0-8% | 0-5% |
| Os | 0-15% | 0-10% | 0-8% | 0-5% |
| Cu | 0-15% | 0-10% | 0-8% | 0-5% |
| Ir | 0-15% | 0-10% | 0-8% | 0-5% |
| Ti | 0-15% | 0-10% | 0-8% | 0-5% |
| Y | 0-15% | 0-10% | 0-8% | 0-5% |
| Zr | 0-15% | 0-10% | 0-8% | 0-5% |
| Ag | 0-15% | 0-10% | 0-8% | 0-5% |
| Al | 0-15% | 0-10% | 0-8% | 0-5% |
| Co | 0-15% | 0-10% | 0-8% | 0-5% |
| Fe | 0-15% | 0-10% | 0-8% | 0-5% |
| Mg | 0-15% | 0-10% | 0-8% | 0-5% |
| Ni | 0-15% | 0-10% | 0-8% | 0-5% |
| Pt | 0-15% | 0-10% | 0-8% | 0-5% |
| Si | 0-15% | 0-10% | 0-8% | 0-5% |
| Sn | 0-15% | 0-10% | 0-8% | 0-5% |
| $Cs_2O$ | 0-1% | 0-1% | 0-1% | 0-1% |
| $La_2O_3$ | 0-1% | 0-1% | 0-1% | 0-1% |
| $Y_2O_3$ | 0-1% | 0-1% | 0-1% | 0-1% |
| $ZrO_2$ | 0-1% | 0-1% | 0-1% | 0-1% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 111 | Ex. 112 | Ex. 113 | Ex. 114 |
|---|---|---|---|---|
| Mo | 40-95% | 40-95% | 40-95% | 40-95% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | ≤1% | ≤1% | ≤1% |
| $La_2O_3$ | 0-2% | 0.1-2% | 0-2% | 0-2% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 5-40% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| Sn | 0-5% | 0-5% | 0-5% | 0-5% |
| CNT | 0-10% | 0-10% | 0-10% | 0-10% |

-continued

| Component/Wt. % | Ex. 115 | Ex. 116 | Ex. 117 |
|---|---|---|---|
| Mo | 40-95% | 40-95% | 40-95% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 5-40% | 5-40% | 5-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/Wt. % | Ex. 118 | Ex. 119 | Ex. 120 |
|---|---|---|---|
| Mo | 60-95% | 60-95% | 60-90% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 5-40% | 5-40% | 10-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| W | 0-50% | 0-50% | 0-50% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/Wt. % | Ex. 121 | Ex. 122 | Ex. 123 | Ex. 124 |
|---|---|---|---|---|
| Mo | 60-95% | 60-95% | 50-95% | 40-80% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2% | 0-2.5% | 0-2.5% |
| $La_2O_3$ | 0-2% | 0.3-0.7% | 0-2% | 0-2% |
| Re | 5-40% | 5-40% | 5-40% | 5-40% |
| Ta | 0-2% | 0-2% | 0-50% | 0-50% |
| W | 0-2% | 0-2% | 0-50% | 20-50% |
| $Y_2O_3$ | 0-1% | 0-1% | 0.3-0.5% | 0-1% |
| $ZrO_2$ | 0-3% | 0-3% | 0-3% | 0-3% |

-continued

| Component/Wt. % | Ex. 125 | Ex. 126 | Ex. 127 |
|---|---|---|---|
| Mo | 97-95% | 50-90% | 60-95% |
| C | 0-0.15% | 0-0.15% | 0-0.15% |
| $Cs_2O$ | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 5-30 | 5-40% | 5-40% |
| Ta | 0-3% | 10-50% | 0-40% |
| W | 0-3% | 0-50% | 0-40% |
| $Y_2O_3$ | 0-1% | 0-1% | 0-1% |
| $ZrO_2$ | 1.2-1.8% | 0-3% | 0-3% |

| Component/Wt. % | Ex. 128 | Ex. 129 | Ex. 130 |
|---|---|---|---|
| W | 20-95% | 60-95% | 20-80% |
| Re | 5-47.5% | 5-40% | 5-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| Ag | 0-5% | 0-5% | 0-5% |
| Al | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | <0.5%. |

| Component/Wt. % | Ex. 131 | Ex. 132 | Ex. 133 | Ex. 134 |
|---|---|---|---|---|
| W | 1-94.9% | 1-94.9% | 1-94.9% | 10-95% |
| Cu | 0.1-94% | 0.1-94% | 0.1-94% | 1-84% |
| C | 0.01-0.3% | 0-0.3% | 0-0.3% | 0-0.3% |
| Co | ≤0.002% | ≤0.002% | ≤0.002% | ≤0.002% |
| $Cs_2O$ | 0-0.2% | 0-0.2% | 0.01-0.2% | 0-0.2% |
| Fe | ≤0.02% | ≤0.02% | ≤0.02% | ≤0.02% |
| H | ≤0.002% | ≤0.002% | ≤0.002% | ≤0.002% |
| Hf | 0.1-2.5% | 0-2.5% | 0-2.5% | 0-2.5% |
| O | ≤0.06% | ≤0.06% | ≤0.06% | ≤0.06% |
| Os | ≤1% | ≤1% | ≤1% | ≤1% |
| $La_2O_3$ | 0-2% | 0.1-2% | 0-2% | 0-2% |
| Mo | 0-5% | 0.1-3% | 0-2% | 0-3% |
| N | ≤20 ppm | ≤20 ppm | ≤20 ppm | ≤20 ppm |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 6-40% |
| S | ≤0.008% | ≤0.008% | ≤0.008% | ≤0.008% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| $Y_2O_3$ | 0-1% | 0-1% | 0.1-1% | 0-1% |
| Zr | ≤1% | ≤1% | ≤1% | ≤1% |
| $ZrO_2$ | 0-3% | 0-3% | 0-3% | 0-3% |
| Ag | 0-5% | 0-5% | 0-5% | 0-5% |
| Al | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |

-continued

| | | | | |
|---|---|---|---|---|
| Si | 0-5% | 0-5% | 0-5% | 0-5% |
| CNT | 0-10% | 0-10% | 0-10% | 0-10% |

| Component/Wt. % | Ex. 135 | Ex. 136 | Ex. 137 |
|---|---|---|---|
| W | 20-96% | 25-92% | 30-88% |
| Cu | 2-74% | 2-68% | 5-62% |
| C | 0-0.3% | 0-0.3% | 0-0.3% |
| Co | ≤0.002% | ≤0.002% | ≤0.002% |
| $Cs_2O$ | 0-0.2% | 0-0.2% | 0-0.2% |
| H | ≤0.002% | ≤0.002% | ≤0.002% |
| Hf | 0-2.5% | 0-2.5% | 0-2.5% |
| O | ≤0.06% | ≤0.06% | ≤0.06% |
| Os | ≤1% | ≤1% | ≤1% |
| $La_2O_3$ | 0-2% | 0-2% | 0-2% |
| Mo | 0-3% | 0-2% | 0-1% |
| N | ≤20 ppm | ≤20 ppm | ≤20 ppm |
| Nb | ≤0.01% | ≤0.01% | ≤0.01% |
| Pt | ≤1% | ≤1% | ≤1% |
| Re | 6-40% | 7-40% | 8-40% |
| S | ≤0.008% | ≤0.008% | ≤0.008% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| $Y_2O_3$ | 0-1% | 0-1% | 0-1% |
| $ZrO_2$ | 0.1-3% | 0-3% | 0-3% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | 0-10% |

| Component/Wt. % | Ex. 138 | Ex. 139 | Ex. 140 | Ex. 141 |
|---|---|---|---|---|
| W | 25-88% | 35-87% | 40-86% | 50-85% |
| Cu | 5-68% | 5-57% | 5-51% | 5-40% |
| C | 0.05-0.15% | 0-0.15% | 0-0.15% | 0-0.15% |
| $Cs_2O$ | 0-0.2% | 0-0.2% | 0.04-0.1% | 0-0.2% |
| Hf | 0.8-1.4% | 0-2.5% | 0-2.5% | 0-2.5% |
| $La_2O_3$ | 7-20% | 8-20% | 9-20% | 10-20% |
| Re | 0-40% | 0-40% | 0-40% | 0-40% |
| Ta | 0-50% | 0-50% | 0-50% | 0-50% |
| $Y_2O_3$ | 0-1% | 0-1% | 0.3-0.5% | 0-1% |
| $ZrO_2$ | 0-3% | 0-3% | 0-3% | 0-3% |

| Component/Wt. % | Ex. 142 | Ex. 143 | Ex. 144 |
|---|---|---|---|
| W | 55-88% | 60-87% | 70-86% |
| Cu | 1-34% | 1-28% | 1-17% |
| C | 0-0.15% | 0-0.15% | 0-0.15% |
| $Cs_2O$ | 0-0.2% | 0-0.2% | 0-0.2% |
| Hf | 0-2.5% | 0-2.5% | 0-2.5% |
| $La_2O_3$ | 0-2% | 0-2% | 0-2% |
| Re | 11-40% | 12-40% | 13-40% |
| Ta | 0-50% | 10-50% | 0-50% |
| W | 0-50% | 0-50% | 0-50% |
| $Y_2O_3$ | 0-1% | 0-1% | 0-1% |
| $ZrO_2$ | 1.2-1.8% | 0-3% | 0-3% |

| Component/Wt. % | Ex. 145 | Ex. 146 | Ex. 147 |
|---|---|---|---|
| Ti | 55-66% | 65-76% | 70-76% |
| Mo | 20-41% | 20-31% | 20-26% |
| Re | 4-20% | 4-20% | 4-20% |
| Yt | <0.5% | <0.5% | <0.5% |
| Nb | <0.5% | <0.5% | <0.5% |
| Co | <0.5% | <0.5% | <0.5% |
| Cr | <0.5% | <0.5% | <0.5% |
| Zr | <0.5% | <0.5% | <0.5% |
| C | ≤0.15% | ≤0.15% | ≤0.15% |
| O | ≤0.06% | ≤0.06% | ≤0.06% |
| N | ≤20 ppm | ≤20 ppm | ≤20 ppm |

-continued

| Component/Wt. % | Ex. 148 | Ex. 149 | Ex. 150 |
|---|---|---|---|
| W | 20-95% | 60-85% | 20-84% |
| Re | 5-47.5% | 15-40% | 5-47.5% |
| Mo | 0-47.5% | <0.5% | 1-47.5% |

| Component/Wt. % | Ex. 151 | Ex. 152 | Ex. 153 |
|---|---|---|---|
| W | 50.1-93% | 65-92% | 70-90% |
| Re | 7-40% | 8-35% | 9-30% |
| Mo | 0-40% | <0.5% | 1-30% |

| Component/Wt. % | Ex. 154 | Ex. 155 | Ex. 156 |
|---|---|---|---|
| W | 20-49% | 20-49% | 20-49% |
| Re | 5-40% | 5-40% | 5-39% |
| Mo | 20-60% | 30-60% | 40-60% |

| Component/Wt. % | Ex. 157 | Ex. 158 | Ex. 159 |
|---|---|---|---|
| W | 20-40% | 20-35% | 20-30% |
| Re | 7-40% | 10-40% | 25-40% |
| Mo | 0-40% | 10-40% | 25-40% |

| Component/Wt. % | Ex. 160 | Ex. 161 | Ex. 162 |
|---|---|---|---|
| W | 20-95% | 60-93% | 20-80% |
| Re | 5-47.5% | 7-40% | 5-47.5% |
| Mo | 0-47.5% | <0.5% | 1-47.5% |
| Cu | <0.5% | <0.5% | <0.5% |
| C | ≤0.15% | ≤0.15% | ≤0.15% |
| Co | ≤0.002% | ≤0.002% | ≤0.002% |
| $Cs_2O$ | ≤0.2% | ≤0.2% | ≤0.2% |
| Fe | ≤0.02% | ≤0.02% | ≤0.02% |
| H | ≤0.002% | ≤0.002% | ≤0.002% |
| Hf | <0.5% | <0.5% | <0.5% |
| $La_2O_3$ | <0.5% | <0.5% | <0.5% |
| O | ≤0.06% | ≤0.06% | ≤0.06% |
| Os | <0.5% | <0.5% | <0.5% |
| N | ≤20 ppm | ≤20 ppm | ≤20 ppm |
| Nb | ≤0.01% | ≤0.01% | ≤0.01% |
| Pt | <0.5% | <0.5% | <0.5% |
| S | ≤0.008% | ≤0.008% | ≤0.008% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| $Y_2O_3$ | <0.5% | <0.5% | <0.5% |
| Zr | <0.5% | <0.5% | <0.5% |
| $ZrO_2$ | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |
| CNT | 0-10% | 0-10% | <0.5% |

| Component/Wt. % | Ex. 163 | Ex. 164 | Ex. 165 | Ex. 166 |
|---|---|---|---|---|
| Ag | 0-10% | 0-10% | 0-10% | 0-10% |
| Al | 0-10% | 0-10% | 0-10% | 2-10% |
| B | 0-10% | 0-10% | 0-10% | 0-10% |
| Bi | 0-10% | 0-10% | 0-10% | 0-10% |
| Cr | 2-30% | 10-30% | 0-20% | 0-20% |
| Cu | 0-10% | 0-10% | 0-10% | 0-10% |
| Co | 0-10% | 32-70% | 0-10% | 0-10% |
| Fe | 50-80% | 0-20% | 0-10% | 0-10% |
| Hf | 0-10% | 0-10% | 0-10% | 0-10% |
| Ir | 0-10% | 0-10% | 0-10% | 0-10% |
| La | 0-10% | 0-10% | 0-10% | 0-10% |
| Mg | 0-10% | 0-10% | 0-10% | 0-10% |
| Mn | 0-20% | 0-10% | 0-10% | 0-10% |
| Mo | 0-10% | 0-30% | 0-16% | 0-16% |
| Nb | 0-10% | 0-10% | 0-10% | 0-10% |
| Ni | 0.1-30% | 0.1-40% | 0-10% | 0-10% |
| Os | 0-10% | 0-10% | 0-10% | 0-10% |
| Pt | 0-10% | 0-10% | 0-10% | 0-10% |

-continued

| | | | | |
|---|---|---|---|---|
| Re | 5-40% | 4.8-40% | 4.5-80% | 4.5-80% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-12% | 0-12% |
| Ta | 0-10% | 0-10% | 0-10% | 0-10% |
| Tc | 0-10% | 0-10% | 0-10% | 0-10% |
| Ti | 0-10% | 0-10% | 70-91.5% | 70-91.5% |
| V | 0-10% | 0-10% | 0-10% | 0.01-10% |
| W | 0-10% | 0-20% | 0-10% | 0-10% |
| Y | 0-10% | 0-10% | 0-10% | 0-10% |
| Zr | 0-10% | 0-10% | 0-10% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 167 | Ex. 168 | Ex. 169 | Ex. 170 |
|---|---|---|---|---|
| Ag | 0-10% | 0-10% | 0-10% | 0-10% |
| Al | 0-10% | 0-10% | 0-10% | 0-10% |
| B | 0-10% | 0-10% | 0-10% | 0-10% |
| Bi | 0-10% | 0-10% | 0-10% | 0-10% |
| Cr | 0-10% | 0-20% | 0-20% | 0-10% |
| Cu | 0-10% | 0-10% | 0-50% | 0-10% |
| Co | 0-10% | 0-10% | 0-10% | 0-10% |
| Fe | 0-10% | 0-10% | 0-10% | 0-10% |
| Hf | 0-10% | 0-10% | 0-10% | 0-10% |
| Ir | 0-10% | 0-10% | 0-10% | 0-12% |
| La | 0-10% | 0-10% | 0-10% | 0-10% |
| Mg | 0-10% | 0-10% | 0-10% | 0-10% |
| Mn | 0-10% | 0-10% | 0-10% | 0-10% |
| Mo | 0-55% | 40-93% | 0-50% | 0-20% |
| Nb | 0-10% | 0-10% | 0-10% | 40-85% |
| Ni | 0-45% | 0-10% | 0-10% | 0-10% |
| Os | 0-10% | 0-10% | 0-10% | 0-10% |
| Pt | 0-10% | 0-10% | 0-10% | 0-10% |
| Re | 14-40% | 7-40% | 7-40% | 7-40% |
| Rh | 0-10% | 0-10% | 0-10% | 0-10% |
| Se | 0-10% | 0-10% | 0-10% | 0-10% |
| Si | 0-10% | 0-10% | 0-10% | 0-10% |
| Sn | 0-10% | 0-10% | 0-10% | 0-10% |
| Ta | 35-84% | 0-50% | 0-50% | 0-35% |
| Tc | 0-10% | 0-10% | 0-10% | 0-10% |
| Ti | 0-10% | 0-10% | 0-10% | 0-10% |
| V | 0-10% | 0-10% | 0-10% | 0-10% |
| W | 0.1-25% | 0-50% | 14-10% | 0-15% |
| Y | 0-10% | 0-10% | 0-10% | 0-10% |
| Zr | 0-10% | 0-10% | 0-50% | 0-10% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 171 | Ex. 172 | Ex. 173 | Ex. 174 |
|---|---|---|---|---|
| Ag | 0-10% | 0-10% | 0-5% | 0-5% |
| Al | 0-10% | 0-10% | 0-5% | 5-7% |
| B | 0-10% | 0-10% | 0-5% | 0-5% |
| Bi | 0-10% | 0-10% | 0-5% | 0-5% |
| Cr | 0-10% | 1-95% | 12-28% | 0-5% |
| Cu | 0-10% | 0-10% | 0-5% | 0-5% |
| Co | 0-10% | 0-10% | 36-68% | 0-5% |
| Fe | 0-10% | 0-10% | 0-18% | 0-5% |
| Hf | 0-10% | 0-10% | 0-5% | 0-5% |
| Ir | 0-10% | 0-10% | 0-5% | 0-5% |
| La | 0-10% | 0-10% | 0-5% | 0-5% |
| Mg | 0-10% | 0-10% | 0-5% | 0-5% |
| Mn | 0-10% | 0-10% | 0-5% | 0-5% |
| Mo | 0-10% | 0-20% | 0-12% | 0-5% |
| Nb | 0-10% | 0-10% | 0-5% | 0-5% |
| Ni | 30-58% | 0-10% | 9-36% | 0-5% |
| Os | 0-10% | 0-10% | 0-5% | 0-5% |

-continued

| | | | | |
|---|---|---|---|---|
| Pt | 0-10% | 0-10% | 0-5% | 0-5% |
| Re | 5-40% | 5-40% | 4.8-40% | 4.5-40% |
| Rh | 0-10% | 0-10% | 0-5% | 0-5% |
| Se | 0-10% | 0-10% | 0-5% | 0-5% |
| Si | 0-10% | 0-10% | 0-5% | 0-5% |
| Sn | 0-10% | 0-10% | 0-5% | 0-5% |
| Ta | 0-10% | 0-10% | 0-5% | 0-5% |
| Tc | 0-10% | 0-10% | 0-5% | 0-5% |
| Ti | 30-58% | 0-40% | 0-5% | 70-91.5% |
| V | 0-10% | 0-10% | 0-5% | 3-6% |
| W | 0-10% | 0-10% | 0-16% | 0-5% |
| Y | 0-10% | 0-10% | 0-5% | 0-5% |
| Zr | 0-10% | 0-20% | 0-5% | 0-5% |
| $Cs_2O$ | 0-1% | 0-1% | 0-1% | 0-1% |
| $La_2O_3$ | 0-3% | 0.1-2% | 0-2% | 0-2% |
| $Y_2O_3$ | 0-1% | 0-1% | 0.1-1% | 0-1% |
| $ZrO_2$ | 0-3% | 0-3% | 0-3% | 0-3% |
| C | <0.06% | <0.06% | <0.06% | <0.06% |
| N | <0.06% | <0.06% | <0.06% | <0.06% |
| O | <0.06% | <0.06% | <0.06% | <0.06% |

| Component/Wt. % | Ex. 175 | Ex. 176 | Ex. 177 | Ex. 178 |
|---|---|---|---|---|
| Ag | 0-8% | 0-8% | 0-8% | 0-8% |
| Al | 0-8% | 0-8% | 0-8% | 2-10% |
| B | 0-8% | 0-8% | 0-8% | 0-8% |
| Bi | 0-8% | 0-8% | 0-8% | 0-8% |
| Cr | 2-30% | 10-30% | 0-20% | 0-20% |
| Cu | 0-8% | 0-8% | 0-8% | 0-8% |
| Co | 0-8% | 32-70% | 0-8% | 0-8% |
| Fe | 50-80% | 0-20% | 0-8% | 0-8% |
| Hf | 0-8% | 0-8% | 0-8% | 0-8% |
| Ir | 0-8% | 0-8% | 0-8% | 0-8% |
| La | 0-8% | 0-8% | 0-8% | 0-8% |
| Mg | 0-8% | 0-8% | 0-8% | 0-8% |
| Mn | 0-20% | 0-8% | 0-8% | 0-8% |
| Mo | 0-8% | 0-30% | 0-16% | 0-16% |
| Nb | 0-8% | 0-8% | 0-8% | 0-8% |
| Ni | 0.1-30% | 0.1-40% | 0-8% | 0-8% |
| Os | 0-8% | 0-8% | 0-8% | 0-8% |
| Pt | 0-8% | 0-8% | 0-8% | 0-8% |
| Re | 5-40% | 4.8-40% | 4.5-80% | 4.5-80% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-12% | 0-12% |
| Ta | 0-8% | 0-8% | 0-8% | 0-8% |
| Tc | 0-8% | 0-8% | 0-8% | 0-8% |
| Ti | 0-8% | 0-8% | 70-91.5% | 70-91.5% |
| V | 0-8% | 0-8% | 0-8% | 0.01-10% |
| W | 0-8% | 0-20% | 0-8% | 0-8% |
| Y | 0-8% | 0-8% | 0-8% | 0-8% |
| Zr | 0-8% | 0-8% | 0-8% | 0-8% |

| Component/Wt. % | Ex. 179 | Ex. 180 | Ex. 181 | Ex. 182 |
|---|---|---|---|---|
| Ag | 0-8% | 0-8% | 0-8% | 0-8% |
| Al | 0-8% | 0-8% | 0-8% | 0-8% |
| B | 0-8% | 0-8% | 0-8% | 0-8% |
| Bi | 0-8% | 0-8% | 0-8% | 0-8% |
| Cr | 0-8% | 0-20% | 0-20% | 0-8% |
| Cu | 0-8% | 0-8% | 0-50% | 0-8% |
| Co | 0-8% | 0-8% | 0-8% | 0-8% |
| Fe | 0-8% | 0-8% | 0-8% | 0-8% |
| Hf | 0-8% | 0-8% | 0-8% | 0-8% |
| Ir | 0-8% | 0-8% | 0-8% | 0-12% |
| La | 0-8% | 0-8% | 0-8% | 0-8% |
| Mg | 0-8% | 0-8% | 0-8% | 0-8% |
| Mn | 0-8% | 0-8% | 0-8% | 0-8% |
| Mo | 0-55% | 40-93% | 0-50% | 0-20% |
| Nb | 0-8% | 0-8% | 0-8% | 40-85% |
| Ni | 0-45% | 0-8% | 0-8% | 0-8% |
| Os | 0-8% | 0-8% | 0-8% | 0-8% |
| Pt | 0-8% | 0-8% | 0-8% | 0-8% |
| Re | 14-40% | 7-40% | 7-40% | 7-40% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-8% | 0-8% |

-continued

| | | | | |
|---|---|---|---|---|
| Ta | 35-84% | 0-50% | 0-50% | 0-35% |
| Tc | 0-8% | 0-8% | 0-8% | 0-8% |
| Ti | 0-8% | 0-8% | 0-8% | 0-8% |
| V | 0-8% | 0-8% | 0-8% | 0-8% |
| W | 0.1-25% | 0-50% | 14-10% | 0-15% |
| Y | 0-8% | 0-8% | 0-8% | 0-8% |
| Zr | 0-8% | 0-8% | 0-50% | 0-8% |

| Component/Wt. % | Ex. 183 | Ex. 184 | Ex. 185 | Ex. 186 |
|---|---|---|---|---|
| Ag | 0-5% | 0-5% | 0-5% | 0-5% |
| Al | 0-5% | 0-5% | 0-5% | 5-7% |
| B | 0-5% | 0-5% | 0-5% | 0-5% |
| Bi | 0-5% | 0-5% | 0-5% | 0-5% |
| Cr | 0-5% | 1-95% | 12-28% | 0-5% |
| Cu | 0-5% | 0-5% | 0-5% | 0-5% |
| Co | 0-5% | 0-5% | 36-68% | 0-5% |
| Fe | 0-5% | 0-5% | 0-18% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-20% | 0-12% | 0-5% |
| Nb | 0-5% | 0-5% | 0-5% | 0-5% |
| Ni | 30-58% | 0-5% | 9-36% | 0-5% |
| Os | 0-5% | 0-5% | 0-5% | 0-5% |
| Pt | 0-5% | 0-5% | 0-5% | 0-5% |
| Re | 5-40% | 5-40% | 4.8-40% | 4.5-40% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 30-58% | 0-40% | 0-5% | 70-91.5% |
| V | 0-5% | 0-5% | 0-5% | 3-6% |
| W | 0-5% | 0-5% | 0-16% | 0-5% |
| Y | 0-5% | 0-5% | 0-5% | 0-5% |
| Zr | 0-5% | 0-20% | 0-5% | 0-5% |

| Component/Wt. % | Ex. 187 | Ex. 188 | Ex. 189 | Ex. 190 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 1-15% | 2-10% | 3-8% | 0-5% |
| Nb | 0-5% | 0-5% | 0-5% | 20-45% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 1-15% |
| Tc | 0-5% | 0-5% | 0-5% | 0-5% |
| Ti | 51-70% | 51-70% | 55-70% | 51-70% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 20-40% | 22-38% | 27-33% | 1-15% |

| Component/Wt. % | Ex. 191 | Ex. 192 | Ex. 193 | Ex. 194 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |

-continued

| | | | | |
|---|---|---|---|---|
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 25-40% | 30-40% | 25-40% | 26-32% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 2-8% | 3-6% | 5-15% | 10-14% |
| Tc | 0-5% | 0-5% | 0-5% | 0-5% |
| Ti | 51-70% | 52-63% | 51-68% | 51-62% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-12% | 4-8% | 2-8% | 2-6% |

| Component/Wt. % | Ex. 195 | Ex. 196 | Ex. 197 | Ex. 198 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 5-35% | 10-30% | 15-25% |
| Cu | 0-5% | 0-5% | 0-5% | 0-5% |
| Co | 0-5% | 20-55% | 25-50% | 35-45% |
| Fe | 0-5% | 3-25% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 2-15% | 3-12% | 4-9% |
| Nb | 30-40% | 0-5% | 0-5% | 0-5% |
| Ni | 0-5% | 4-23% | 5-20% | 10-18% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 1-3% | 0-5% | 0-5% | 0-5% |
| Tc | 0-5% | 0-5% | 0-5% | 0-5% |
| Ti | 51-67% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-5% | 0-5% | 0-5% | 0-5% |

| Component/Wt. % | Ex. 199 | Ex. 200 | Ex. 201 | Ex. 202 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 30-65% | 40-60% | 45-55% | 0-5% |
| Nb | 0-5% | 0-5% | 0-5% | 55-99.75% |
| Ni | 0-5% | 0-5% | 0-5% | 0-5% |

-continued

| | | | | |
|---|---|---|---|---|
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 30-56% | 40-60% | 45-55% | 0.25-45% |

| Component/Wt. % | Ex. 203 | Ex. 204 | Ex. 205 | Ex. 206 |
|---|---|---|---|---|
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 75-99.5% | 95-99.25% | 55-78.5% | 68-74.25% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 20-35% | 25-30% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 1-8% | 0-5% |
| Y | 0-5% | 0-5% | 0-5% | 0-5% |
| Zr | 0.5-25% | 0.75-5% | 0.5-5% | 0.75-3% |

| Element/Wt. % | Ex. 207 | Ex. 208 | Ex. 209 | Ex. 210 |
|---|---|---|---|---|
| Re | 30-75% | 40-75% | 45-75% | 45-70% |
| Cr | 25-70% | 25-65% | 25-55% | 30-55% |
| Mo | 0-25% | 0-25% | 1-25% | 2-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| C | <0.06% | <0.06% | <0.06% | <0.06% |
| N | <0.06% | <0.06% | <0.06% | <0.06% |
| O | <0.06% | <0.06% | <0.06% | <0.06% |

In Examples 1-210, it will be appreciated that all of the above ranges include any value between the range and any other range that is between the ranges set forth above. Any of the above values that include the ≤symbol includes the range from 0 to the stated value and all values and ranges therebetween.

In accordance with another and/or alternative aspect of the present disclosure, the metal alloy includes at least 15 awt. % (e.g., 10-99 awt. % and all values and ranges therebetween) of the metal alloy includes rhenium. In one non-limiting embodiment, the metal alloy includes at least 15 awt. % (e.g., 15-99.9 awt. % and all values and ranges therebetween) rhenium, and 0.1-95.5 wt. % (and all values and ranges therebetween) of one or more additives selected from the group of aluminum, boron, beryllium, bismuth, cadmium, calcium, cerium, cerium oxide, chromium, cobalt, copper, gallium, gold, hafnium, iridium, iron, lanthanum, lanthanum oxide, lead, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, yttrium oxide, zinc, zirconium, and/or zirconium oxide. In another non-limiting embodiment, the metal alloy includes at least 20 awt. % (e.g., 20-99.9 awt. % and all values and ranges therebetween) rhenium, and 0.1-94 wt. % (and all values and ranges therebetween) of one or more additives selected from the group of aluminum, boron, beryllium, bismuth, cadmium, calcium, cerium, cerium oxide, chromium, cobalt, copper, gallium, gold, hafnium, iridium, iron, lanthanum, lanthanum oxide, lead, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, yttrium oxide, zinc, zirconium, and/or zirconium oxide, and the metal alloy includes 0-2 wt. % (and all values and ranges therebetween) of a combination of other metals, carbon, oxygen, phosphorous, sulfur, hydrogen and nitrogen.

In accordance with another and/or alternative aspect of the present disclosure, the metal alloy includes 35-75 wt. % (e.g., and all values and ranges therebetween) of the metal alloy includes rhenium, and 25-65 wt. % (and all values and ranges therebetween) of the metal alloy includes two or more of aluminum, boron, beryllium, bismuth, cadmium, calcium, cerium, cerium oxide, chromium, cobalt, copper, gallium, gold, hafnium, iridium, iron, lanthanum, lanthanum oxide, lead, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, yttrium oxide, zinc, zirconium, and/or zirconium oxide, and the metal alloy includes 0-2 wt. % of a combination of other combination of other metals, carbon, oxygen, phosphorous, sulfur, hydrogen and nitrogen. In one non-limiting embodiment, the metal alloy includes 50-75 wt. % rhenium, 24-49 wt. % chromium, 1-15 wt. % molybdenum, and 0-25 wt. % one or more of aluminum, boron, beryllium, bismuth, cadmium, calcium, cerium, cerium oxide, cobalt, copper, gallium, gold, hafnium, iridium, iron, lanthanum, lanthanum oxide, lead, lithium, magnesium, manganese, nickel, niobium, osmium, palladium, platinum, rare earth metals, rhodium, ruthenium, scandium, silver, silicon, tantalum, technetium, tin, titanium, tungsten, vanadium, yttrium, yttrium oxide, zinc, zirconium, and/or zirconium oxide, and the metal alloy includes 0-2 wt. % of a combination of other metals, carbon, oxygen, phosphorous, sulfur, hydrogen and nitrogen.

In accordance with another and/or alternative aspect of the present disclosure, the metal alloy includes rhenium and molybdenum, and the weight percent of rhenium in the metal alloy is greater that the weight percent of molybdenum in the metal alloy. In one non-limiting embodiment, the metal alloy includes rhenium and molybdenum, and the weight percent of rhenium in the metal alloy is greater that the weight percent of molybdenum in the metal alloy, and the weight percent of one or more of bismuth, niobium, tantalum, tungsten, titanium, vanadium, chromium, manganese, yttrium, zirconium, technetium, ruthenium, rhodium, hafnium, osmium, copper, and iridium in the metal alloy is greater that the weight percent of molybdenum in the metal alloy. In another non-limiting embodiment, the metal alloy includes rhenium and molybdenum, and the weight percent of rhenium in the metal alloy is greater that the weight percent of molybdenum in the metal alloy, and the weight percent of one or more of bismuth, niobium, tantalum, tungsten, titanium, vanadium, chromium, manganese, yttrium, zirconium, technetium, ruthenium, rhodium, hafnium, osmium, copper, and iridium in the metal alloy is greater that the weight percent of molybdenum in the metal alloy, and the weight percent of molybdenum in the metal alloy is 0.1-15 wt. % (and all values and ranges therebetween). In another non-limiting embodiment, the metal alloy includes rhenium and molybdenum, and the weight percent of rhenium in the metal alloy is greater that the weight percent of molybdenum in the metal alloy, and the weight percent of one or more of bismuth, niobium, tantalum, tungsten, titanium, vanadium, chromium, manganese, yttrium, zirconium, technetium, ruthenium, rhodium, hafnium, osmium, copper, and iridium in the metal alloy is greater that the weight percent of molybdenum in the metal alloy, and the weight percent of molybdenum in the metal alloy is 0.1-15 wt. %, and the metal alloy includes 0-2 wt. % of a combination of other metals, carbon, oxygen, phosphorous, sulfur, hydrogen and nitrogen.

In accordance with another and/or alternative aspect of the present disclosure, the metal alloy includes rhenium and molybdenum, and the weight percent of rhenium plus the weigh percent of the combined weight percentage of bismuth, niobium, tantalum, tungsten, titanium, vanadium, chromium, manganese, yttrium, zirconium, technetium, ruthenium, rhodium, hafnium, osmium, copper, and iridium in the metal alloy is greater than the weight percent of molybdenum. In one specific non-limiting formulation, the metal alloy includes rhenium and molybdenum, and the weight percent of rhenium plus the weigh percent of the combined weight percentage of bismuth, chromium, iridium, niobium, tantalum, titanium, yttrium, and zirconium in the metal alloy is greater than the weight percent of molybdenum. In another specific non-limiting formulation, the metal alloy includes rhenium and molybdenum, and the weight percent of rhenium plus the weigh percent of the combined weight percentage of chromium, niobium, tantalum, and zirconium in the metal alloy is greater than the weight percent of molybdenum. In another non-limiting specific non-limiting formulation, the metal alloy includes rhenium and molybdenum, and the weight percent of molybdenum in the metal alloy is at least 10 wt. % and less than 50 wt. % (and all values and ranges therebetween), and 0-25 wt. % (and all values and ranges therebetween) of one or more of aluminum, bismuth, calcium, cerium oxide, cobalt, copper, gold, hafnium, iridium, iron, lanthanum, lanthanum oxide, lead, magnesium, manganese, nickel, niobium, osmium, platinum, rare earth metals, rhodium, ruthenium, silver, silicon, tantalum, technetium, tin, titanium, tungsten, vanadium, yttrium, yttrium oxide, zinc, zirconium, and/or zirconium oxide, and the metal alloy includes 0-2 wt. % of a combination of other metals, carbon, oxygen, phosphorous, sulfur, hydrogen and nitrogen. In another non-limiting specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of bismuth, niobium, tantalum, tungsten, titanium, vanadium, chromium, manganese, yttrium, zirconium, technetium, ruthenium, rhodium, hafnium, osmium, copper, and iridium in the metal alloy is 11-41 wt. % (and all values and ranges therebetween). In another non-limiting specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of bismuth, chromium, iridium, niobium, tantalum, titanium, yttrium, and zirconium in the metal alloy is 11-41 wt. % (and all values and ranges therebetween). In another non-limiting specific non-limiting formulation, the weight percent of rhenium in the metal alloy is 41-58.5 wt. % (and all values and ranges therebetween), the weight percent of molybdenum in the metal alloy is at least 15-45 wt. % (and all values and ranges therebetween), and the combined weight percent of chromium, niobium, tantalum, and zirconium in the metal alloy is 11-41 wt. % (and all values and ranges therebetween). In another non-limiting embodiment of the invention, the weight percent of rhenium in the metal alloy is greater than the combined weight percent of bismuth, chromium, iridium, niobium, tantalum, titanium, yttrium, and zirconium in the metal alloy. In another non-limiting specific non-limiting formulation, the weight percent of rhenium in the metal alloy is greater than the combined weight percent of chromium, niobium, tantalum, and zirconium in the metal alloy.

In accordance with another and/or alternative aspect of the present disclosure, the metal alloy includes rhenium and molybdenum, and the atomic weight percent of rhenium to the atomic weight percent of the combination of bismuth, niobium, tantalum, tungsten, titanium, vanadium, chromium, manganese, yttrium, zirconium, technetium, ruthenium, rhodium, hafnium, osmium, copper, and iridium is 0.7:1 to 1.5:1 (and all values and ranges therebetween), typically 0.8:1 to 1.4:1, more typically 0.8:1 to 1.25:1, and still more typically about 0.9:1 to 1.1:1 (e.g., 1:1). In one specific non-limiting formulation, the metal alloy includes rhenium and molybdenum, and the atomic weight percent of rhenium to the atomic weight percent of the combination of bismuth, chromium, iridium, niobium, tantalum, titanium, yttrium, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1). In another specific non-limiting formulation, the metal alloy includes rhenium and molybdenum, and the atomic weight percent of rhenium to the atomic weight percent of the combination of chromium, niobium, tantalum, and zirconium is 0.7:1 to 5.1:1 (and all values and ranges therebetween), typically 0.8:1 to 1.5:1, more typically 0.8:1 to 1.25:1, and still more typically about 0.9:1 to 1.1:1 (e.g., 1:1).

In accordance with another and/or alternative aspect of the present disclosure, the metal alloy includes rhenium and molybdenum, and the metal alloy includes at least 15 awt. % rhenium and two additional metals selected from bismuth, niobium, tantalum, tungsten, titanium, vanadium, chromium, manganese, yttrium, zirconium, technetium, ruthenium, rhodium, hafnium, osmium, copper, and iridium, the atomic ratio of the two additional metals is 0.4:1 to 2.5:1 (and all values and ranges therebetween), and typically 0.5:1 to 2:1. In one specific non-limiting formulation, the metal alloy includes rhenium and molybdenum, and the metal alloy includes at least 15 awt. % rhenium and two of bismuth, chromium, iridium, niobium, tantalum, titanium, yttrium, and zirconium, and the atomic ratio of the two metals is 0.4:1 to 2.5:1 (and all values and ranges therebetween), and typically 0.5:1 to 2:1. In another specific non-limiting formulation, the metal alloy includes rhenium and molybdenum, and the metal alloy includes at least 15 awt. % rhenium and two of chromium, niobium, tantalum, and zirconium, the atomic ratio of the two metals is 0.4:1 to 2.5:1 (and all values and ranges therebetween), and typically 0.5:1 to 2:1. In another non-limiting embodiment, the metal alloy includes rhenium, molybdenum and chromium.

In accordance with another and/or alternative aspect of the present disclosure, the metal alloy is formed of at least 15 awt. % rhenium plus at least two metals selected from the group of molybdenum, bismuth, chromium, iridium, niobium, tantalum, titanium, yttrium, and zirconium, and the content of the metal alloy that includes other elements and compounds is 0-0.1 wt. %, typically 0-0.01 wt. %, and more typically 0-0.001 wt. %. In another specific non-limiting formulation, the metal alloy is formed of at least 15 awt. % rhenium plus at least three metals selected form the group of molybdenum, chromium, niobium, tantalum, and zirconium, and the content of the metal alloy that includes other elements and compounds is 0-0.1 wt. %, typically 0-0.01 wt. %, and more typically 0-0.001 wt. %. In another non-limiting embodiment, the metal alloy includes rhenium, molybdenum, and chromium.

In accordance with another and/or alternative aspect of the present disclosure, the metal alloy includes at least 35 wt. % (e.g., 35-75 wt. % and all values and ranges therebetween) rhenium, and the metal alloy also includes chromium. In one non-limiting embodiment, the metal alloy includes at least 35 wt. % rhenium and at least 25 wt. % (e.g., 25-49.9 wt. % and all values and ranges therebetween) of the metal alloy includes chromium. In another non-limiting embodiment, the metal alloy includes at least 35 wt. % rhenium and at least 30 wt. % of the metal alloy includes chromium. In another non-limiting embodiment, the metal alloy includes at least 35 wt. % rhenium and at least 33 wt. % of the metal alloy includes chromium. In another non-limiting embodiment, at least 50 wt. % (e.g., 50-74.9 wt. % and all values and ranges therebetween) of the metal alloy includes rhenium, at least 25 wt. % (e.g., 25-49.9 wt. % and all values and ranges therebetween) of the metal alloy includes chromium, and 0.1-25 wt. % (and all values and ranges therebetween) of the metal alloy includes one or more of aluminum, bismuth, calcium, carbon, cerium oxide, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silver, tantalum, technetium, titanium, tungsten, vanadium, yttrium, yttrium oxide, zinc, zirconium, and/or zirconium oxide. In another non-limiting embodiment, at least 50 wt. % (e.g., 50-74.9 wt. % and all values and ranges therebetween) of the metal alloy includes rhenium, at least 25 wt. % (e.g., 25-49.9 wt. % and all values and ranges therebetween) of the metal alloy includes chromium, and 0.1-25 wt. % (and all values and ranges therebetween) of the metal alloy includes one or more of aluminum, bismuth, calcium, carbon, cerium oxide, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silver, tantalum, technetium, titanium, tungsten, vanadium, yttrium, yttrium oxide, zinc, zirconium, and/or zirconium oxide, and the metal alloy includes 0-2 wt. % of a combination of other metals, carbon, oxygen, phosphorous, sulfur, hydrogen and nitrogen. In another non-limiting embodiment, at least 55 wt. % (e.g., 55-69.9 wt. % and all values and ranges therebetween) of the metal alloy includes rhenium, at least 30 wt. % (e.g., 30-44.9 wt. % and all values and ranges therebetween) of the metal alloy includes chromium, and 0.1-15 wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium, and the metal alloy includes 0-2 wt. % of a combination of other metals, carbon, oxygen, phosphorous, sulfur, hydrogen and nitrogen.

In accordance with another and/or alternative aspect of the present disclosure, the metal alloy includes 15-60 atomic weight percent rhenium (and all values and ranges therebetween) and one or more metals selected from the group consisting of molybdenum, chromium, tantalum, niobium, titanium, and zirconium. In another non-limiting embodiment, the metal alloy includes 15-60 awt. % rhenium and one or more metals selected from the group consisting of 0.5-70 awt. % chromium (and all values and ranges therebetween), 0.5-70 awt. % tantalum (and all values and ranges therebetween), 0.5-70 at. % niobium (and all values and ranges therebetween), 0.5-70 awt. % titanium (and all values and ranges therebetween), 0.5-70 awt. % zirconium (and all values and ranges therebetween), and 0.5-70 awt. % molybdenum (and all values and ranges therebetween).

In accordance with another and/or alternative aspect of the present disclosure, the metal alloy includes 15-50 awt. % rhenium (and all values and ranges therebetween) and 0.5-70 awt. % chromium (and all values and ranges therebetween).

In accordance with another and/or alternative aspect of the present disclosure, the metal alloy includes 15-50 awt. % rhenium (and all values and ranges therebetween) and 0.5-70 awt. % tantalum (and all values and ranges therebetween).

In accordance with another and/or alternative aspect of the present disclosure, the metal alloy includes 15-50 awt. % rhenium (and all values and ranges therebetween) and 0.5-70 awt. % niobium (and all values and ranges therebetween).

In accordance with another and/or alternative aspect of the present disclosure, the metal alloy includes 15-50 awt. % rhenium (and all values and ranges therebetween) and 0.5-70 awt. % titanium (and all values and ranges therebetween).

In accordance with another and/or alternative aspect of the present disclosure, the metal alloy includes 15-50 awt. % rhenium (and all values and ranges therebetween) and 0.5-70 awt. % zirconium (and all values and ranges therebetween).

In accordance with another and/or alternative aspect of the present disclosure, the metal alloy includes 15-50 awt. % rhenium (and all values and ranges therebetween) and 0.5-70 awt. % molybdenum (and all values and ranges therebetween).

In accordance with another and/or alternative aspect of the present disclosure, the metal alloy includes at least 15 awt. % rhenium, greater than 50 wt. % titanium (e.g., 51-80 wt. % and all values and ranges therebetween), 15-45 wt. % (and all values and ranges therebetween) niobium, 1-10% wt. % (and all values and ranges therebetween) zirconium, and 1-15 wt. % (and all values and ranges therebetween) tantalum. In one non-limiting formulation, the metal alloy includes at least 15 awt. % rhenium, 58-70 wt. % titanium, 27-37 wt. % niobium, 2-9 wt. % zirconium, and 1-15 wt. % tantalum.

In accordance with another and/or alternative aspect of the present disclosure, the metal alloy includes at least 15 awt. % rhenium, greater than 50 wt. % titanium (e.g., 51-80 wt. % and all values and ranges therebetween), 15-45 wt. % (and all values and ranges therebetween) niobium, and 1-10% wt. % (and all values and ranges therebetween) molybdenum. In one non-limiting formulation, the metal alloy includes at least 15 awt. % rhenium, 58-69 wt. % titanium, 27-33 wt. % niobium, and 4-8 wt. % molybdenum.

In accordance with another and/or alternative aspect of the present disclosure, the metal alloy includes at least 15 awt. % rhenium, 30-60 wt. % cobalt (and all values and ranges therebetween), 10-30 wt. % chromium (and all values and ranges therebetween), 5-20 wt. % iron (and all values and ranges therebetween), 5-22 wt. % nickel (and all values and ranges therebetween), and 2-12 wt. % molybdenum (and all values and ranges therebetween). In one non-limiting formulation, the metal alloy includes at least 15 awt. % rhenium, 35-45 wt. % cobalt, 15-25 wt. % chromium, 12-20 wt. % iron, 10-20% wt. % nickel, and 5-9 wt. % molybdenum.

In accordance with another and/or alternative aspect of the present disclosure, the metal alloy includes at least 15 awt. % rhenium, 30-60 wt. % zirconium (and all values and ranges therebetween), and 30-60 wt. % molybdenum (and all values and ranges therebetween). In one non-limiting formulation, the metal alloy includes at least 15 awt. % rhenium, 35-55 wt. % cobalt, and 35-55 wt. % molybdenum.

In accordance with another and/or alternative aspect of the present disclosure, the metal alloy includes at least 15 awt. % rhenium, 80-95 wt. % niobium (and all values and ranges therebetween), and 0.5-10 wt. % zirconium (and all values and ranges therebetween). In one non-limiting formulation, the metal alloy includes at least 15 awt. % rhenium, 85-95 wt. % niobium, and 0.75-4 wt. % niobium.

In accordance with another and/or alternative aspect of the present disclosure, the metal alloy includes at least 15 awt. % rhenium, 55-75 wt. % niobium (and all values and ranges therebetween), 18-40 wt. % tantalum (and all values and ranges therebetween), 1-7 wt. % tungsten (and all values and ranges therebetween), and 0.5-4 wt. % zirconium (and all values and ranges therebetween). In one non-limiting formulation, the metal alloy includes at least 15 awt. % rhenium, 60-70 wt. % niobium, 24-32 wt. % tantalum, 2-5 wt. % tungsten, and 0.75-3 wt. % zirconium.

In accordance with another and/or alternative aspect of the present disclosure, the metal alloy, which can optionally be used to partially or fully form a medical device, includes 38-60 wt. % rhenium (and all values and ranges therebetween), 29 wt. % to less than 50 wt. % molybdenum (and all values and ranges therebetween), and 10-30 wt. % additive metal (and all values and ranges therebetween); wherein a combined content of rhenium and molybdenum constitutes 70-90 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes one or more metals selected from the group of bismuth, niobium, tantalum, tungsten, titanium, vanadium, chromium, manganese, yttrium, zirconium, technetium, ruthenium, rhodium, hafnium, osmium, copper, and iridium; and wherein an atomic ratio of rhenium to total content of additive material in the metal alloy is optionally 0.8:1 to 1.25:1 (and all values and ranges therebetween).

In accordance with another and/or alternative aspect of the present disclosure, the metal alloy, which can optionally be used to partially or fully form a medical device, includes 40-55 wt. % rhenium (and all values and ranges therebetween), 30-46 wt. % molybdenum (and all values and ranges therebetween), and 12-20 wt. % additive metal (and all values and ranges therebetween); wherein a combined content of rhenium and molybdenum constitutes 80-88 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes one or more metals selected from the group of bismuth, niobium, tantalum, tungsten, titanium, vanadium, chromium, manganese, yttrium, zirconium, technetium, ruthenium, rhodium, hafnium, osmium, copper, and iridium; and wherein an atomic ratio of rhenium to total content of additive material in the metal alloy is optionally 0.8:1 to 1.25:1 (and all values and ranges therebetween).

In accordance with another and/or alternative aspect of the present disclosure, the metal alloy, which can optionally be used to partially or fully form a medical device, includes 38-60 wt. % rhenium (and all values and ranges therebetween), 29 wt. % to less than 50 wt. % molybdenum (and all values and ranges therebetween), and 10-30 wt. % additive metal (and all values and ranges therebetween); wherein a combined content of rhenium and constitutes 70-90 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes chromium and optionally one or more metals selected from the group of bismuth, niobium, tantalum, tungsten, titanium, vanadium, manganese, yttrium, zirconium, technetium, ruthenium, rhodium, hafnium, osmium, copper, and iridium; and wherein an atomic ratio of rhenium to total content of additive material in the metal alloy is optionally 0.8:1 to 1.25:1 (and all values and ranges therebetween).

In accordance with another and/or alternative aspect of the present disclosure, the metal alloy, which can optionally be used to partially or fully form a medical device, includes 40-55 wt. % rhenium (and all values and ranges therebetween), 30-46 wt. % molybdenum (and all values and ranges therebetween), and 12-20 wt. % additive metal (and all values and ranges therebetween); wherein a combined content of rhenium and molybdenum constitutes 80-88 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes chromium and one or more metals selected from the group of bismuth, niobium, tantalum, tungsten, titanium, vanadium, manganese, yttrium, zirconium, technetium, ruthenium, rhodium, hafnium, osmium, copper, and iridium; and wherein an atomic ratio of rhenium to total content of additive material in the metal alloy is optionally 0.8:1 to 1.25:1 (and all values and ranges therebetween).

In accordance with another and/or alternative aspect of the present disclosure, the metal alloy, which can optionally be used to partially or fully form a medical device, includes 38-60 wt. % rhenium (and all values and ranges therebetween), 29 wt. % to less than 50 wt. % molybdenum (and all values and ranges therebetween), and 10-30 wt. % additive metal (and all values and ranges therebetween); wherein a combined content of rhenium and molybdenum constitutes 70-90 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes chromium and optionally one or more metals selected from the group of niobium, tantalum, and zirconium; and wherein an atomic ratio of rhenium to total content of additive material in the metal alloy is optionally 0.8:1 to 1.25:1.

In accordance with another and/or alternative aspect of the present disclosure, the metal alloy, which can optionally be used to partially or fully form a medical device, includes 38-60 wt. % rhenium (and all values and ranges therebetween), 29 wt. % to less than 50 wt. % molybdenum (and all values and ranges therebetween), and 10-30 wt. % additive metal (and all values and ranges therebetween); wherein a combined content of rhenium and molybdenum constitutes 70-90 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes chromium and one or more metals selected from the group of bismuth, niobium, tantalum, tungsten, titanium, vanadium, manganese, yttrium, zirconium, technetium, ruthenium, rhodium, hafnium, osmium, copper, and iridium; and wherein an atomic ratio of rhenium to total content of additive material in the metal alloy is optionally 0.8:1 to 1.25:1 (and all values and ranges therebetween).

In accordance with another and/or alternative aspect of the present disclosure, the metal alloy, which can optionally be used to partially or fully form a medical device, includes 38-60 wt. % rhenium (and all values and ranges therebetween), 29 wt. % to less than 50 wt. % molybdenum (and all values and ranges therebetween), and 10-30 wt. % additive metal (and all values and ranges therebetween); wherein a combined content of rhenium and molybdenum constitutes 70-90 wt. % (and all values and ranges therebetween) of the metal alloy; wherein a combined content of rhenium, molybdenum and additive metal constitutes 99-100 wt. % (and all values and ranges therebetween) of the metal alloy; wherein said metal additive includes chromium and one or more metals selected from the group of niobium, tantalum, and zirconium; and wherein an atomic ratio of rhenium to total content of additive material in the metal alloy is optionally 0.8:1 to 1.25:1 (and all values and ranges therebetween).

In accordance with another and/or alternative aspect of the present disclosure, at least 30 wt. % (e.g., 30-100 wt. % and all values and ranges therebetween) of the metal alloy includes one or more of molybdenum, niobium, rhenium, tantalum, or tungsten, and the metal alloy includes at least 15 awt. % rhenium. In another non-limiting embodiment, at least 40 wt. % of the metal alloy includes one or more of molybdenum, niobium, rhenium, tantalum, or tungsten. In another non-limiting embodiment, at least 50 wt. % of the metal alloy includes one or more of molybdenum, niobium, rhenium, tantalum, or tungsten, and the metal alloy includes at least 15 awt. % rhenium.

In accordance with another and/or alternative aspect of the present disclosure, at least 50 wt. % (e.g., 50-100 wt. % and all values and ranges therebetween) of the metal alloy includes one or more of molybdenum, niobium, rhenium, tantalum, or tungsten, and the metal alloy includes at least 15 awt. % rhenium, and 0-40 wt. % (and all values and ranges therebetween) of the metal alloy includes one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide. In another non-limiting embodiment, at least 50 wt. % (e.g., 50-99.9 wt. % and all values and ranges therebetween) of the metal alloy includes one or more of molybdenum, niobium, rhenium, tantalum, or tungsten, and the metal alloy includes at least 15 awt. % rhenium, and 0.1-40 wt. % (and all values and ranges therebetween) of the metal alloy includes one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide. In another non-limiting embodiment, at least 50 wt. % (e.g., 50-100 wt. % and all values and ranges therebetween) of the metal alloy includes one or more of molybdenum, niobium, rhenium, tantalum, or tungsten, and the metal alloy includes at least 15 awt. % rhenium, and 0-40 wt. % (and all values and ranges therebetween) of the metal alloy includes one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-2 wt. % (and all values and ranges therebetween) of a combination of other metals, carbon, oxygen, phosphorous, sulfur, hydrogen and nitrogen. In another non-limiting embodiment, at least 50 wt. % (e.g., 50-99.9 wt. % and all values and ranges therebetween) of the metal alloy includes one or more of molybdenum, niobium, rhenium, tantalum, or tungsten, and the metal alloy includes at least 15 awt. % rhenium, and 0.1-40 wt. % (and all values and ranges therebetween) of the metal alloy includes one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-2 wt. % (and all values and ranges therebetween) of a combination of other metals, carbon, oxygen, phosphorous, sulfur, hydrogen and nitrogen. In another non-limiting embodiment, at least 55 wt. % of the metal alloy includes one or more of molybdenum, niobium, rhenium, tantalum, or tungsten, and the metal alloy includes at least 15 awt. % rhenium, and 0-40 wt. % of the metal alloy includes one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-0.1 wt. % of a combination of other metals, carbon, oxygen, phosphorous, sulfur, hydrogen and nitrogen. In another non-limiting embodiment, at least 55 wt. % of the metal alloy includes one or more of molybdenum, niobium, rhenium, tantalum, or tungsten, and the metal alloy includes at least 15 awt. % rhenium, and 0.1-40 wt. % of the metal alloy includes one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-0.1 wt. % of a combination of other metals, carbon, oxygen, phosphorous, sulfur, hydrogen and nitrogen.

In accordance with another and/or alternative aspect of the present disclosure, the metal alloy includes at least 30 wt. % (e.g., 30-99 wt. % and all values and ranges therebetween) rhenium and one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide. In another non-limiting embodiment, the metal alloy includes at least 30 wt. % (e.g., 30-99 wt. % and all values and ranges therebetween) rhenium and one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-2 wt. % (and all values and ranges therebetween) of a combination of other metals, carbon, oxygen, and nitrogen. In another non-limiting embodiment, the metal alloy includes at least 30 wt. % (e.g., 30-99 wt. % and all values and ranges therebetween) rhenium and one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-0.1 wt. % (and all values and ranges therebetween) of a combination of other metals, carbon, oxygen, and nitrogen. In another non-limiting embodiment, the metal alloy includes at least 35 wt. % (e.g., 35-99 wt. % and all values and ranges therebetween) rhenium and 0.1-65 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide. In another non-limiting embodiment, the metal alloy includes at least 35 wt. % (e.g., 35-99 wt. % and all values and ranges therebetween) rhenium and 0.1-65 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-2 wt. % (and all values and ranges therebetween) of a combination of other metals, carbon, oxygen, and nitrogen. In another non-limiting embodiment, the metal alloy includes at least 35 wt. % (e.g., 35-99.9 wt. % and all values and ranges therebetween) rhenium and 0.1-65 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-0.1 wt. % (and all values and ranges therebetween) of a combination of other metals, carbon, oxygen, and nitrogen. In another non-limiting embodiment, the metal alloy includes at least 40 wt. % (e.g., 40-99.9 wt. % and all values and ranges therebetween) rhenium and 0.1-60 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide. In another non-limiting embodiment, the metal alloy includes at least 40 wt. % (e.g., 40-99.9 wt. % and all values and ranges therebetween) rhenium and 0.1-60 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-2 wt. % (and all values and ranges therebetween) of a combination of other metals, carbon, oxygen, and nitrogen. In another non-limiting embodiment, the metal alloy includes at least 40 wt. % (e.g., 40-99.9 wt. % and all values and ranges therebetween) rhenium and 0.1-60 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, and zirconium oxide, and the metal alloy includes 0-0.1 wt. % (and all values and ranges therebetween) of a combination of other metals, carbon, oxygen, and nitrogen.

In accordance with another and/or alternative aspect of the present disclosure, there is provided a metal alloy wherein at least 20 wt. % (e.g., 20-99 wt. % and all values and ranges therebetween) of the metal alloy includes rhenium. In one non-limiting embodiment, the metal alloy includes at least 20 wt. % (e.g., 20-99.9 wt. % and all values and ranges therebetween) rhenium, and 0.1-80 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes at least 20 wt. % (e.g., 30-99.9 wt. % and all values and ranges therebetween) rhenium, and 0.1-80 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes at least 30 wt. % (e.g., 30-99.9 wt. % and all values and ranges therebetween) rhenium, and 0.1-70 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes at least 30 wt. % (e.g., 30-99.9 wt. % and all values and ranges therebetween) rhenium, and 0.1-70 wt. % (and all values and ranges therebetween) of one or more of copper, chromium, hafnium, iridium, manganese, molybdenum, niobium, osmium, rhodium, ruthenium, tantalum, technetium, titanium, tungsten, vanadium, zirconium, and/or alloys of one or more of such components. In another non-limiting embodiment, the metal alloy includes at least 35 wt. % (e.g., 35-99.9 wt. % and all values and ranges therebetween) rhenium, and 0.1-65 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes at least 35 wt. % (e.g., 35-99.9 wt. % and all values and ranges therebetween) rhenium, and 0.1-65 wt. % (and all values and ranges therebetween) of one or more of copper, chromium, hafnium, iridium, manganese, molybdenum, niobium, osmium, rhodium, ruthenium, tantalum, technetium, titanium, tungsten, vanadium, zirconium, and/or alloys of one or more of such components. In another non-limiting embodiment, In another non-limiting embodiment, the metal alloy includes 35-60 wt. % (and all values and ranges therebetween) rhenium, and 40-65 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes 35-60 wt. % (and all values and ranges therebetween) rhenium, and 40-65 wt. % (and all values and ranges therebetween) of one or more of copper, chromium, hafnium, iridium, manganese, molybdenum, niobium, osmium, rhodium, ruthenium, tantalum, technetium, titanium, tungsten, vanadium, zirconium, and/or alloys of one or more of such components. In another non-limiting embodiment, the metal alloy includes at least 40 wt. % (e.g., 40-99.9 wt. % and all values and ranges therebetween) rhenium, and 0.1-60 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes at least 40 wt. % (e.g., 40-99.9 wt. % and all values and ranges therebetween) rhenium, and 0.1-60 wt. % (and all values and ranges therebetween) of one or more of copper, chromium, hafnium, iridium, manganese, molybdenum, niobium, osmium, rhodium, ruthenium, tantalum, technetium, titanium, tungsten, vanadium, zirconium, and/or alloys of one or more of such components. In one non-limiting embodiment, the metal alloy includes at least 50 wt. % (e.g., 50-99.9 wt. % and all values and ranges therebetween) rhenium, and 0.1-50 wt. % (and all values and ranges therebetween) of one or more of aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, tungsten, vanadium, yttrium, yttrium oxide, zinc, zirconium, zirconium oxide, and/or alloys of one or more of such components. In another non-limiting embodiment, the metal alloy includes at least 50 wt. % (e.g., 50-99.9 wt. % and all values and ranges therebetween) rhenium, and 0.1-50 wt. % (and all values and ranges therebetween) of one or more of copper, chromium, hafnium, iridium, manganese, molybdenum, niobium, osmium, rhodium, ruthenium, tantalum, technetium, titanium, tungsten, vanadium, zirconium, and/or alloys of one or more of such components.

In accordance with another and/or alternative aspect of the present disclosure, the metals used to form the metal alloy includes at least 15 awt. % rhenium and tungsten and optionally one or more alloying agents such as, but not limited to, aluminum, bismuth, calcium, carbon, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silicon, silver, tantalum, technetium, tin, titanium, vanadium, yttrium, yttrium oxide, zinc, zirconium, and zirconium oxide of one or more of such components (e.g., WRe, WReMo, etc.). Although the metal alloy is described as including one or more metals and/or metal oxides, it can be appreciated that some of the metals and/or metal oxides in the metal alloy can be substituted for one or more materials selected from the group of ceramics, plastics, thermoplastics, thermosets, rubbers, laminates, non-wovens, etc. In one non-limiting formulation, the metal alloy includes at least 15 awt. % rhenium and up to 40 wt. % rhenium and at least 60 wt. % tungsten. In one non-limiting embodiment, the total weight percent of the tungsten and rhenium in the tungsten-rhenium alloy is at least about 95 wt. %, typically at least about 99 wt. %, more typically at least about 99.5 wt. %, yet more typically at least about 99.9 wt. %, and still more typically at least about 99.99 wt. %. In another non-limiting formulation, the metal alloy includes at least 15 awt. % rhenium and up to 47.5 wt. % rhenium and at least 20-80 wt. % tungsten (and all values and ranges therebetween) and 1-47.5 wt. % molybdenum (and all values and ranges therebetween). The total weight percent of the tungsten, rhenium, and molybdenum in the tungsten-rhenium-molybdenum alloy is at least about 95 wt. %, typically at least about 99 wt. %, more typically at least about 99.5 wt. %, yet more typically at least about 99.9 wt. %, and still more typically at least about 99.99 wt. %. In one non-limiting specific tungsten-rhenium-molybdenum alloy, the weight percent of the tungsten is greater than a weight percent of rhenium and also greater than the weight percent of molybdenum. In another non-limiting specific tungsten-rhenium-molybdenum alloy, the weight percent of the tungsten is greater than 50 wt. % of the tungsten-rhenium-molybdenum alloy. In another non-limiting specific tungsten-rhenium-molybdenum alloy, the weight percent of the tungsten is greater than a weight percent of rhenium, but less than a weigh percent of molybdenum. In another non-limiting specific tungsten-rhenium-molybdenum alloy, the weight percent of the tungsten is greater than a weight percent of molybdenum, but less than a weigh percent of rhenium. In another non-limiting specific tungsten-rhenium-molybdenum alloy, the weight percent of the tungsten is less than a weight percent of rhenium and also less than the weight percent of molybdenum.

In accordance with another and/or alternative aspect of the present disclosure, there is provided a metal alloy wherein at least 30 wt. % (e.g., 30-99 wt. % and all values and ranges therebetween) of the metal alloy includes rhenium. In another non-limiting embodiment, at least 35 wt. % of the metal alloy includes rhenium. In another non-limiting embodiment, at least 35 wt. % (e.g., 35-99.9 wt. % and all values and ranges therebetween) of the metal alloy includes rhenium, and 0.1-65 wt. % (and all values and ranges therebetween) of the metal alloy includes one or more of molybdenum, niobium, tantalum, tantalum, titanium, vanadium, chromium, manganese, zirconium, technetium, ruthenium, rhodium, hafnium, osmium, copper, and/or iridium. In another non-limiting embodiment, 35-60 wt. % (and all values and ranges therebetween) of the metal alloy includes rhenium, and 40-65 wt. % (and all values and ranges therebetween) of the metal alloy includes one or more of molybdenum, niobium, tantalum, tungsten, titanium, vanadium, chromium, manganese, zirconium, technetium, ruthenium, rhodium, hafnium, osmium, copper, and/or iridium. In another non-limiting embodiment, 35-60 wt. % (e.g., and all values and ranges therebetween) of the metal alloy includes rhenium, and 40-65 wt. % (and all values and ranges therebetween) of the metal alloy includes two or more of molybdenum, niobium, tantalum, tantalum, titanium, vanadium, chromium, manganese, zirconium, technetium, ruthenium, rhodium, hafnium, osmium, copper, and/or iridium. In another non-limiting embodiment, 35-60 wt. % (e.g., and all values and ranges therebetween) of the metal alloy includes rhenium, and 40-65 wt. % (and all values and ranges therebetween) of the metal alloy includes three or more of molybdenum, niobium, tantalum, tantalum, titanium, vanadium, chromium, manganese, zirconium, technetium, ruthenium, rhodium, hafnium, osmium, copper, and/or iridium.

In accordance with another and/or alternative aspect of the present disclosure, the metals used to form the metal alloy include at least 35 wt. % rhenium (e.g., 35-99.9 wt. % and all values and ranges therebetween) and one or more alloying agents such as, but are not limited to, molybdenum, niobium, tantalum, tantalum, titanium, vanadium, chromium, manganese, zirconium, technetium, ruthenium, rhodium, hafnium, osmium, copper, and/or iridium, and/or alloys of one or more of such components. In one non-limiting formulation, the metal alloy includes 40-99.9 wt. % rhenium and one or more molybdenum, niobium, tantalum, tantalum, titanium, vanadium, chromium, manganese, zirconium, technetium, ruthenium, rhodium, hafnium, osmium, copper, and/or iridium. In one non-limiting formulation, the metal alloy includes rhenium and one or more molybdenum, niobium, tantalum, tantalum, titanium, vanadium, chromium, manganese, zirconium, technetium, ruthenium, rhodium, hafnium, osmium, copper, and/or iridium.

In accordance with another and/or alternative aspect of the present disclosure, the metals used to form the metal alloy include at least 15 awt. % rhenium, molybdenum, and one or more alloying metals selected from the group consisting of bismuth, chromium, copper, hafnium, iridium, manganese, niobium, osmium, rhodium, ruthenium, tantalum, technetium, titanium, tungsten, vanadium, yttrium, and zirconium. In one non-limiting embodiment, a combined weight percentage of rhenium and alloy metals in the metal alloy is greater than or equal to the weight percent of molybdenum in the metal alloy. In another non-limiting embodiment, a combined weight percentage of rhenium and alloy metals in the metal alloy is greater than the weight percent of molybdenum in the metal alloy. In another non-limiting embodiment, a weight percent of molybdenum in the metal alloy is at least 10 wt. % and less than 60 wt. % (and all values and ranges therebetween). In another non-limiting embodiment, a weight percent of rhenium in the metal alloy is 35-60 wt. % (and all values and ranges therebetween). In another non-limiting embodiment, a combined weight percent of the alloying metals is 5-45 wt. % (and all values and ranges therebetween) of the metal alloy. In another non-limiting embodiment, a weight percent of the rhenium in the metal alloy is greater than a combined weight percent of the alloying metals. In another non-limiting embodiment, a combined weight percent of the rhenium, molybdenum, and the one or more alloying metals in the metal alloy is at least 99.9 wt. %. In another non-limiting embodiment, the alloying metal includes chromium. In another non-limiting embodiment, the alloying metal includes chromium and one or more metals selected from the group consisting of bismuth, zirconium, iridium, niobium, tantalum, titanium, and yttrium. In another non-limiting embodiment, the alloying metal includes chromium and one or more metals selected from the group consisting of bismuth, zirconium, iridium, niobium, tantalum, titanium, and yttrium; and wherein an atomic ratio of chromium to an atomic ratio of each or all of the metals selected from the group consisting of bismuth, chromium, iridium, niobium, tantalum, titanium, and yttrium is 0.4:1 to 2.5:1 (and all values and ranges therebetween). In another non-limiting embodiment, the alloying metal includes chromium and one or more metals selected from the group consisting of zirconium, niobium, and tantalum. In another non-limiting embodiment, the alloying metal includes a first metal selected from the group consisting of bismuth, chromium, iridium, niobium, tantalum, titanium, yttrium and zirconium, and a second metal selected from the group consisting of bismuth, chromium, iridium, niobium, tantalum, titanium, yttrium and zirconium; and wherein the first and second metals are different; and wherein an atomic ratio of the first metal to the second metal is 0.4:1 to 2.5:1 (and all values and ranges therebetween). In another non-limiting embodiment, the alloying metal a first metal selected from the group consisting of chromium, niobium, tantalum, and zirconium, and a second metal selected from the group consisting of chromium, niobium, tantalum, and zirconium; and wherein the first and second metals are different; and wherein an atomic ratio of the first metal to the second metal is 0.4:1 to 2.5:1 (and all values and ranges therebetween).

In accordance with another and/or alternative aspect of the present disclosure, at least 35 wt. % (e.g., 35-75 wt. % and all values and ranges therebetween) of the metal alloy includes rhenium, and the metal alloy also includes chromium. In one non-limiting embodiment, at least 25 wt. % (e.g., 25-49.9 wt. % and all values and ranges therebetween) of the metal alloy includes chromium. In another non-limiting embodiment, at least 30 wt. % of the metal alloy includes chromium. In another non-limiting embodiment, at least 33 wt. % of the metal alloy includes chromium. In another non-limiting embodiment, at least 50 wt. % (e.g., 50-74.9 wt. % and all values and ranges therebetween) of the metal alloy includes rhenium, at least 25 wt. % (e.g., 25-49.9 wt. % and all values and ranges therebetween) of the metal alloy includes chromium, and 0.1-25 wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 55 wt. % (e.g., 55-69.9 wt. % and all values and ranges therebetween) of the metal alloy includes rhenium, at least 30 wt. % (e.g., 30-44.9 wt. % and all values and ranges therebetween) of the metal alloy includes chromium, and 0.1-15 wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 60 wt. % (e.g., 60-69.9 wt. % and all values and ranges therebetween) of the metal alloy includes rhenium, at least 30 wt. % (e.g., 30-39.9 wt. % and all values and ranges therebetween) of the metal alloy includes chromium, and 0.1-10% wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium. In another non-limiting embodiment, at least 62 wt. % (e.g., 62-67.9 wt. % and all values and ranges therebetween) of the metal alloy includes rhenium, at least 32 wt. % (e.g., 32-32.9 wt. % and all values and ranges therebetween) of the metal alloy includes chromium, and 0.1-6 wt. % (and all values and ranges therebetween) of the metal alloy includes one or more of molybdenum, bismuth, niobium, tantalum, titanium, vanadium, tungsten, manganese, zirconium, technetium, ruthenium, rhodium, hafnium, osmium, copper, yttrium, zirconium, and/or iridium.

In accordance with another and/or alternative aspect of the present disclosure, the metal alloy optionally includes less than about 5 wt. % (e.g., 0-4.999999 wt. % and all values and ranges therebetween) other metals and/or impurities, typically 0-1 wt. %, more typically 0-0.1 wt. %, even more typically 0-0.01 wt. %, and still even more typically 0-0.001 wt. %. A high purity level of the metal alloy results in the formation of a more homogeneous alloy, which in turn results in a more uniform density throughout the metal alloy, and also results in the desired yield and ultimate tensile strengths of the metal alloy. In one specific non-limiting formulation, the metal alloy is formed of rhenium plus at least one additive selected form the group of aluminum, bismuth, calcium, cerium oxide, chromium, cobalt, copper, gold, hafnium, iridium, iron, lanthanum, lanthanum oxide, lead, magnesium, manganese, molybdenum, nickel, niobium, osmium, platinum, rare earth metals, rhodium, ruthenium, silver, silicon, tantalum, technetium, tin, titanium, tungsten, vanadium, yttrium, yttrium oxide, zinc, zirconium, and/or zirconium oxide, and the content of the metal alloy that includes other elements and compounds is 0-0.1 wt. %, typically 0-0.01 wt. %, and more typically 0-0.001 wt. %.

In accordance with another and/or alternative aspect of the present disclosure, there is provided a medical device (e.g., stent, prosthetic heart valve, etc.) that is at least partially formed of a metal alloy and is configured to be radially collapsible to a collapsed or crimped state for introduction into the body on a delivery catheter and radially expandable to an expanded state for implanting the prosthetic heart valve at a desired location in the body (e.g., blood vessel, heart, ureter, bile duct, pancreatic duct, esophagus, lung, eyes, sinus, oral stent, etc.). The frame of the medical device can be formed of a plastically-expandable material that permits crimping of the frame to a smaller profile for delivery and expansion of the medical device using an expansion device such as the balloon of a balloon catheter.

In accordance with another and/or alternative aspect of the present disclosure, there is provided a medical device including a frame that can be optionally coated with a polymer material (e.g., silicone, PTFE, ePTFE, polyurethane, polyolefins, hydrogels, biological materials (e.g., pericardium or biological polymers such as collagen, gelatin, or hyaluronic acid derivatives), etc.). The coating can be used to partially or fully encapsulate the struts on the frame and/or to fill in the openings between the struts.

In accordance with another and/or alternative aspect of the present disclosure, the metal alloy used to form at least a portion of the medical device has one or more improved properties (e.g., strength, durability, hardness, biostability, bendability, coefficient of friction, radial strength, flexibility, tensile strength, tensile elongation, longitudinal lengthening, stress-strain properties, reduced recoil, radiopacity, heat sensitivity, biocompatibility, improved fatigue life, crack resistance, crack propagation resistance, reduced magnetic susceptibility, etc.), improved conformity when bent, less recoil, increased yield strength, improved fatigue ductility, improved durability, improved fatigue life, reduced adverse tissue reactions, reduced metal ion release, reduced corrosion, reduced allergic reaction, improved hydrophilicity, reduced toxicity, reduced thickness of metal component, improved bone fusion, and/or lower ion release into tissue. These one or more improved physical properties of the metal alloy can be achieved in the medical device without having to increase the bulk, volume, and/or weight of the medical device and, in some instances, these improved physical properties can be obtained even when the volume, bulk, and/or weight of the medical device is reduced as compared to medical devices at least partially formed from standard stainless steel, standard titanium alloy, or standard cobalt and chromium alloy materials.

The metal alloy used to at least partially form the medical device can thus 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the recoil properties of the medical device, 10) improve the biostability and/or biocompatibility properties of the medical device, 11) increase fatigue resistance of the medical device, 12) resist cracking in the medical device and resist propagation of crack, 13) enable smaller, thinner, and/or lighter weight medical device to be made, 14) reduce the outer diameter of a crimped medical device, 15) improve the conformity of the medical device to the shape of the treatment area when the medical device is used and/or expanded in the treatment area, 16) reduce the amount of recoil of the medical device to the shape of the treatment area when the medical device is expanded in the treatment area, 17) increase yield strength of the medical device, 18) improve fatigue ductility of the medical device, 18) improve durability of the medical device, 19) improve fatigue life of the medical device, 20) reduce adverse tissue reactions after implant of the medical device, 21) reduce metal ion release after implant of the medical device, 22) reduce corrosion of the medical device after implant of the medical device, 23) reduce allergic reaction after implant of the medical device, 24) improve hydrophilicity of the medical device, 25) reduce thickness of metal component of medical device, 26) improve bone fusion with medical device, 27) lower ion release from medical device into tissue, 28) reduce magnetic susceptibility of the medical device when implanted in a patient, and/or 29) reduce toxicity of the medical device after implant of the medical device.

The medical device is optionally subjected to one or more manufacturing processes. These manufacturing processes can include, but are not limited to, expansion, laser cutting, etching, crimping, annealing, drawing, pilgering, electroplating, electro-polishing, machining, plasma coating, 3D printed coatings, chemical vapor deposition, chemical polishing, cleaning, pickling, ion beam deposition or implantation, sputter coating, vacuum deposition, etc.

In accordance with another and/or alternative aspect of the present disclosure, the metal alloy optionally includes a certain amount of carbon and oxygen; however, this is not required. These two elements have been found to affect the forming properties and brittleness of the metal alloy. The controlled atomic ratio of carbon and oxygen of the metal alloy also minimize the tendency of the metal alloy to form micro-cracks during the forming of the metal alloy at least partially into a medical device, and/or during the use and/or expansion of the medical device in a body. The control of the atomic ratio of carbon to oxygen in the metal alloy allows for the redistribution of oxygen in the metal alloy to minimize the tendency of micro-cracking in the metal alloy during the forming of the metal alloy at least partially into a medical device, and/or during the use and/or expansion of the medical device in a body. The atomic ratio of carbon to oxygen in the metal alloy is believed to facilitate in minimizing the tendency of micro-cracking in the metal alloy and improve the degree of elongation of the metal alloy, both of which can affect one or more physical properties of the metal alloy that are useful or desired in forming and/or using the medical device. The carbon to oxygen atomic ratio can be as low as about 0.2:1 (e.g., 0.2:1 to 50:1 and all values and ranges therebetween). In one non-limiting formulation, the carbon to oxygen atomic ratio in the metal alloy is generally at least about 0.3:1. Typically the carbon content of the metal alloy is less than about 0.1 wt. % (e.g., 0-0.0999999 wt. % and all values and ranges therebetween), and more typically 0-0.01 wt. %. Carbon contents that are too large can adversely affect the physical properties of the metal alloy. Generally, the oxygen content is to be maintained at very low level. In one non-limiting formulation, the oxygen content is less than about 0.1 wt. % of the metal alloy (e.g., 0-0.0999999 wt. % and all values and ranges therebetween), and typically 0-0.01 wt. %. It is believed that the metal alloy will have a very low tendency to form microcracks during the formation of the medical device and after the medical device has been inserted into a patient by closely controlling the carbon to oxygen ration when the oxygen content exceeds a certain amount in the metal alloy. In one non-limiting arrangement, the carbon to oxygen atomic ratio in the metal alloy is at least about 2.5:1 when the oxygen content is greater than about 100 ppm in the metal alloy of the metal alloy.

In accordance with another and/or alternative aspect of the present disclosure, the metal alloy optionally includes a controlled amount of nitrogen; however, this is not required. Large amounts of nitrogen in the metal alloy can adversely affect the ductility of the metal alloy. This can in turn adversely affect the elongation properties of the metal alloy. A too high nitrogen content in the metal alloy can begin to cause the ductility of the metal alloy to unacceptably decrease, thus adversely affect one or more physical properties of the metal alloy that are useful or desired in forming and/or using the medical device. In one non-limiting formulation, the metal alloy includes less than about 0.001 wt. % nitrogen (e.g., 0 wt. % to 0.0009999 wt. % and all values and ranges therebetween). It is believed that the nitrogen content should be less than the content of carbon or oxygen in the metal alloy. In one non-limiting formulation, the atomic ratio of carbon to nitrogen is at least about 1.5:1 (e.g., 1.5:1 to 400:1 and all values and ranges therebetween). In another non-limiting formulation, the atomic ratio of oxygen to nitrogen is at least about 1.2:1 (e.g., 1.2:1 to 150:1 and all value and ranges therebetween).

In accordance with another and/or alternative aspect of the present disclosure, the medical device is generally designed to include at least about 5 wt. % of the metal alloy (e.g., 5-100 wt. % and all values and ranges therebetween). In one non-limiting embodiment of the disclosure, the medical device includes at least about 50 wt. % of the metal alloy. In another non-limiting embodiment of the disclosure, the medical device includes at least about 95 wt. % of the metal alloy. In one specific configuration, when the medical device includes an expandable frame, the expandable frame is formed of 50-100 wt. % (and all values and ranges therebetween) of the metal alloy, and typically 75-100 wt. % of the metal alloy.

In still another and/or alternative non-limiting aspect of the present invention, the novel metal alloy that is used to form all or part of the medical device 1) is not clad, metal sprayed, plated and/or formed (e.g., cold worked, hot worked, etc.) onto another metal, or 2) does not have another metal or metal alloy metal sprayed, plated, clad and/or formed onto the novel metal alloy. It will be appreciated that in some applications, the novel metal alloy of the present invention may be clad, metal sprayed, plated and/or formed onto another metal, or another metal or metal alloy may be plated, metal sprayed, clad and/or formed onto the novel metal alloy when forming all or a portion of a medical device.

In yet another and/or alternative non-limiting aspect of the present invention, the novel alloy can be used to form a) a coating on a portion of all of a medical device, or b) a core of a portion or all of a medical device. In one non-limiting embodiment, the novel alloy can be used as a coating on articulation points of artificial joints. Such a coating can provide the benefit of better wear, scratch resistance, and/or elimination of leaching harmful metallic ions (i.e., Co, Cr, etc.) from the articulating surfaces when they undergo fretting (i.e., scratching during relative motion). As can be appreciated, the novel alloy can have other or additional advantages. As can also be appreciated, the novel alloy can be coated on other or additional types of medical devices (e.g., spinal rods, stents, etc.). The composition of the novel alloy coating is different from the composition of the material surface to which the novel alloy is coated. The coating thickness of the novel alloy is non-limiting (e.g., 1 μm to 1 inch and all values and ranges therebetween). In one non-limiting example, there is provided a medical device in the form of a clad rod wherein the core of the rod is formed of a metal or novel alloy (e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.) or ceramic or composite material, and the other layer of the clad rod is formed of the novel alloy. The core and the other layer of the rod can each form 10-99% (and all values and ranges therebetween) of the overall cross section of the rod. The novel alloy coating can be used to create a hard surface on the medical device at specific locations as well as all over the surface. The base hardness of novel alloy can be as low as 300 Vickers and/or as high as 500 Vickers (and all values and ranges therebetween). In instances where the properties of fully annealed material are desired, but only the surface requires to be hardened, the present disclosure includes a method that can provide benefits of both a softer metal alloy with a harder outer surface or shell. A non-limiting example is an orthopedic screw where a softer iron alloy is desired for high ductility as well as ease of machinability. Simultaneously, a hard shell is desired for a finished screw. While the inner hardness can range from 250 Vickers to 550 Vickers (and all values and ranges therebetween), the outer hardness can vary from 350 Vickers to 1000 Vickers (and all values and ranges therebetween) when using novel alloy. As can be appreciated, other inner and outer hardness values can be used for the medical device.

In another non-limiting embodiment, the medical device can be in the form of a rod. The core of the rod can be formed of the novel alloy and then the outside of the core can then be coated with one or more other materials (e.g., another type of metal or novel alloy [e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.), polymer coating, ceramic coating, composite material coating, etc.). Such a rod can be used, for example, for orthopedic applications such as, but not limited to, spinal rods and/or pedicle screw systems. Non-limiting benefits of using the novel alloy in the core of a medical device can include reducing the size of the medical device, increasing the strength of the medical device, and/or maintaining or reducing the cost of the medical device. As can be appreciated, the novel alloy can have other or additional advantages. As can also be appreciated, the novel alloy can form the core of other or additional types of medical devices. The core size and/or thickness of the novel alloy are non-limiting. In one non-limiting example, there is provided a medical device in the form of a clad rod wherein the core of the rod is formed of a novel alloy, and the other layer of the clad rod is formed of a different metal composition (e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.). The core and the other layer of the rod can each form 10-99% (and all values and ranges therebetween) of the overall cross section of the rod. As can also be appreciated, the novel alloy can form the core of other or additional types of medical devices.

In accordance with another and/or alternative aspect of the present disclosure, the medical device can optionally be formed from a tube or rod of refractory metal, or be formed into a shape that is at least 80% of the final net shape of the medical device.

In accordance with another and/or alternative aspect of the present disclosure, the metal alloy has several physical properties that positively affect the medical device when the medical device is at least partially formed of the metal alloy of the present disclosure. In one non-limiting embodiment of the disclosure, the average Vickers hardness of the metal alloy of the present disclosure used to at least partially form the medical device is optionally at least about 150 Vickers (e.g., 150-300 Vickers and all values and ranges therebetween), and typically 160-240 Vickers; however, this is not required. The metal alloy of the present disclosure generally has an average hardness that is greater than standard stainless steel. In another and/or alternative non-limiting embodiment of the disclosure, the average ultimate tensile strength of the metal alloy of the present disclosure is optionally at least about 125 ksi (e.g., 125-300 ksi and all values and ranges therebetween); however, this is not required. In another and/or alternative non-limiting embodiment of the disclosure, the average yield strength of the metal alloy of the present disclosure is optionally at least about 100 ksi (e.g., 100-275 ksi and all values and ranges therebetween); however, this is not required. In another and/or alternative non-limiting embodiment of the disclosure, the average grain size of the metal alloy of the present disclosure used to at least partially form the medical device is optionally no greater than about 4 ASTM (e.g., 4 ASTM to 20 ASTM using ASTM E112 and all values and ranges therebetween, e.g., 0.35 micron to 90 micron, and all values and ranges therebetween). The small grain size of the metal alloy of the present disclosure enables the medical device to have the desired elongation and ductility properties useful in enabling the medical device to be formed, crimped, and/or expanded.

In another and/or alternative non-limiting embodiment of the disclosure, the average tensile elongation of the metal alloy of the present disclosure used to at least partially form the medical device is optionally at least about 25% (e.g., 25-50% average tensile elongation and all values and ranges therebetween). An average tensile elongation of at least 25% for the metal alloy is useful to facilitate in the medical device being properly expanded when positioned in the treatment area of a body. A medical device that does not have an average tensile elongation of at least about 25% may be more prone to the formation of micro-cracks and/or break during the forming, crimping, and/or expansion of the medical device. The unique combination of the metals in the metal alloy of the present disclosure in combination with achieving the desired purity and composition of the alloy and the desired grain size of the metal alloy results in 1) a medical device having the desired high ductility at about room temperature, 2) a medical device having the desired amount of tensile elongation, 3) a homogeneous or solid solution of a metal alloy having high radiopacity, 4) a reduction or prevention of micro-crack formation and/or breaking of the metal alloy of the present disclosure tube when the tube is sized and/or cut to form the medical device, 5) a reduction or prevention of micro-crack formation and/or breaking of the medical device when the device is crimped, 6) a reduction or prevention of micro-crack formation and/or breaking of the medical device when the medical device is bent and/or expanded in a body, 7) a medical device having the desired ultimate tensile strength and yield strength, 8) a medical device having very thin wall thicknesses and still having the desired radial forces needed to retain the medical device on an open state when expanded, 9) a medical device that exhibits less recoil when the medical device is crimped onto a delivery system and/or expanded in a body, 10) a medical device that exhibits improved conformity to the shape of the treatment area in the body when the medical device is expanded in a body, 11) a medical device that exhibits improved fatigue ductility, and/or 12) a medical device that exhibits improved durability.

In accordance with another and/or alternative aspect of the present disclosure, the metal alloy is optionally at least partially formed by a swaging process; however, this is not required. In one non-limiting embodiment, swaging is performed on the metal alloy to at least partially or fully achieve final dimensions of one or more portions of the medical device. The swaging dies can be shaped to fit the final dimension of the medical device; however, this is not required. Where there are undercuts of hollow structures in the medical device (which is not required), a separate piece of metal can be placed in the undercut to at least partially fill the gap. The separate piece of metal (when used) can be designed to be later removed from the undercut; however, this is not required. The swaging operation can be performed on the medical device in the areas to be hardened. For a round or curved portion of a medical device, the swaging can be rotary. For non-round portion of the medical device, the swaging of the non-round portion of the medical device can be performed by non-rotating swaging dies. The dies can optionally be made to oscillate in radial and/or longitudinal directions instead of or in addition to rotating. The medical device can optionally be swaged in multiple directions in a single operation or in multiple operations to achieve a hardness in desired location and/or direction of the medical device. Swaging temperatures for a particular metal alloy can vary. For a metal alloy, the swaging temperature can be from room temperature (RT) (e.g., 10-27° C. and all values and ranges therebetween) to about 400° C. (e.g., 10-400° C. and all values and ranges therebetween) if the swaging is conducted in air or an oxidizing environment. The swaging temperature can be increased to up to about 1500° C. (e.g., 10-15%00° C. and all values and ranges therebetween) if the swaging process is performed in a controlled neutral or non-reducing environment (e.g., inert environment). The swaging process can be conducted by repeatedly hammering the medical device at the location to be hardened at the desired swaging temperature. In one non-limiting embodiment, during the swaging process ions of boron and/or nitrogen are allowed to impinge upon rhenium atoms in the metal alloys that include rhenium so as to form $ReB_2$, $ReN_2$ and/or $ReN_3$; however, this is not required. It has been found that $ReB_2$, $ReN_2$ and/or $ReN_3$ are ultra-hard compounds. In one non-limiting process, the metal for the medical device can be machined and shape into the medical device when the metal is in a less hardened state. As such, the raw starting material can be first annealed to soften and then machined the metal into a desired shape. After the metal alloy is shaped, the metal alloy can be re-hardened. The hardening of the metal alloy of the medical device improves the wear resistance and/or shape retention of the medical device. The metal alloy of the medical generally cannot be re-hardened by annealing, thus a special rehardening processes is required. Such rehardening can be achieved by the swaging process of the present disclosure.

In accordance with another and/or alternative aspect of the present disclosure, the metal alloy can optionally be nitrided; however, this is not required. The nitrided layer on the metal alloy can function as a lubricating surface during the optional drawing of the metal alloy when partially or fully forming the medical device. After the metal alloy is nitrided, the metal alloy is typically cleaned; however, this is not required. During the nitriding process, the surface of the metal alloy is modified by the presence of nitrogen. The nitriding process can be by gas nitriding, salt bath nitriding, or plasma nitriding. In gas nitriding, the nitrogen diffuses onto the surface of the metal alloy, thereby creating a nitrided layer. The thickness and phase constitution of the resulting nitriding layers can be selected and the process optimized for the particular properties required. The metal alloy can optionally be exposed to argon and/or hydrogen gas prior to the nitriding process to clean and/or preheat the metal alloy. These gases can be optionally used to clean oxide layers and/or solvents from the surface of the metal alloy. During the nitriding process, the metal alloy can optionally be exposed to hydrogen gas to inhibit or prevent the formation of oxides on the surface of the metal alloy. The thickness of the nitrided surface layer is less than about 1 mm. In one non-limiting embodiment, the thickness of the nitride surface layer is at least about 50 nanometer and less than about 1 mm (and all values and ranges therebetween). In another non-limiting embodiment, the thickness of the nitrided surface layer is at least about 50 nanometer and less than about 0.1 mm. Generally, the weight percent of nitrogen in the nitrided surface layer is 0.0001-5 wt. % nitrogen (and all values and ranges therebetween). In one non-limiting embodiment, the weight percent of nitrogen in the nitrided surface layer is generally less than one of the primary components of the metal alloy, and typically less than each of the two primary components of the metal alloy. For example, when a metal alloy is nitrided, the weight percent of the nitrogen in the nitrided surface layer is less than a weight percent of the rhenium in the nitrided surface layer. In one non-limiting composition of the nitrided surface layer on a metal alloy (e.g., 47-55 wt. % rhenium, 10-46 wt. % molybdenum, 0.1-30 wt. % additional metal alloying agent), the nitrided surface layer comprises at least 40 wt. % rhenium, at least 8 wt. % molybdenum, and 0.0001-5 wt. % nitrogen (and all values and ranges therebetween). The nitriding process for the metal alloy can be used to increase surface hardness and/or wear resistance of the medical device, and/or to inhibit or prevent discoloration of the metal alloy (e.g., discoloration by oxidation, etc.). For example, the nitriding process can be used to increase the wear resistance of articulation surface or surfaces wear on the metal alloy used in the medical device to extend the life of the medical device, and/or increase the wear life of mating surfaces on the medical device (e.g., polyethylene liners of joint implants like knees, hips, shoulders, etc.), and/or to reduce particulate generation from use of the medical device, and/or to maintain the outer surface appearance of the metal alloy on the medical device.

In accordance with another and/or alternative aspect of the present disclosure, the metal alloy, just prior to or after being partially or fully formed into the desired medical device, can optionally be cleaned, polished, sterilized, nitrided, etc., for final processing of the metal alloy. In one non-limiting embodiment of the disclosure, the metal alloy is electropolished. In one non-limiting aspect of this embodiment, the metal alloy is cleaned prior to being exposed to the polishing solution; however, this is not required.

In accordance with another and/or alternative aspect of the present disclosure, the medical device can optionally contain and/or be coated with one or more agents that facilitate in the success of the medical device and/or treated area. The term "agent" includes, but is not limited to, a substance, pharmaceutical, biologic, veterinary product, drug, and analogs or derivatives otherwise formulated and/or designed to prevent, inhibit, and/or treat one or more clinical and/or biological events, and/or to promote healing. Non-limiting examples of clinical events that can be addressed by one or more agents include, but are not limited to, viral, fungus and/or bacterial infection; vascular diseases and/or disorders, digestive diseases and/or disorders, reproductive diseases and/or disorders, lymphatic diseases and/or disorders, cancer, implant rejection, pain, nausea, swelling, arthritis, bone diseases and/or disorders, organ failure, immunity diseases and/or disorders, cholesterol problems, blood diseases and/or disorders, lung diseases and/or disorders, heart diseases and/or disorders, brain diseases and/or disorders, neuralgia diseases and/or disorders, kidney diseases and/or disorders, ulcers, liver diseases and/or disorders, intestinal diseases and/or disorders, gallbladder diseases and/or disorders, pancreatic diseases and/or disorders, psychological disorders, respiratory diseases and/or disorders, gland diseases and/or disorders, skin diseases and/or disorders, hearing diseases and/or disorders, oral diseases and/or disorders, nasal diseases and/or disorders, eye diseases and/or disorders, fatigue, genetic diseases and/or disorders, burns, scarring and/or scars, trauma, weight diseases and/or disorders, addiction diseases and/or disorders, hair loss, cramp, muscle spasms, tissue repair, nerve repair, neural regeneration, and/or the like. The type and/or amount of agent included in the medical device and/or coated on medical device can vary. When two or more agents are included in and/or coated on the medical device, the amount of the two or more agents can be the same or different. The one or more agents can be coated on and/or impregnated in the medical device by a variety of mechanisms such as, but not limited to, spraying (e.g., atomizing spray techniques, etc.), flame spray coating, powder deposition, dip coating, flow coating, dip-spin coating, roll coating (direct and reverse), sonication, brushing, plasma deposition, depositing by vapor deposition, MEMS technology, and rotating mold deposition. In another and/or alternative non-limiting embodiment of the disclosure, the type and/or amount of agent included on, in, and/or in conjunction with the medical device is generally selected for the treatment of one or more medical treatments. The amount of two or more agents on, in, and/or used in conjunction with the medical device can be the same or different. The one or more agents, when used on and/or in the medical device, can optionally be released in a controlled manner so the area in question to be treated is provided with the desired dosage of agent over a sustained period of time. As can be appreciated, controlled release of one or more agents on the medical device is not always required and/or desirable. As such, one or more of the agents on and/or in the medical device can be uncontrollably released from the medical device during and/or after insertion of the medical device in the treatment area. It can also be appreciated that one or more agents on and/or in the medical device can be controllably released from the medical device and one or more agents on and/or in the medical device can be uncontrollably released from the medical device. It can also be appreciated that one or more agents on and/or in one region of the medical device can be controllably released from the medical device and one or more agents on and/or in the medical device can be uncontrollably released from another region on the medical device. As such, the medical device can be designed such that 1) all the agent on and/or in the medical device is controllably released, 2) some of the agent on and/or in the medical device is controllably released and some of the agent on the medical device is non-controllably released, or 3) none of the agent on and/or in the medical device is controllably released. The medical device can also be designed such that the rate of release of the one or more agents from the medical device is the same or different. The medical device can also be designed such that the rate of release of the one or more agents from one or more regions on the medical device is the same or different. Non-limiting arrangements that can be used to control the release of one or more agents from the medical device include 1) at least partially coating one or more agents with one or more polymers, 2) at least partially incorporating and/or at least partially encapsulating one or more agents into and/or with one or more polymers, and/or 3) inserting one or more agents in pores, passageway, cavities, etc., in the medical device and at least partially coat or cover such pores, passageway, cavities, etc., with one or more polymers. As can be appreciated, other or additional arrangements can be used to control the release of one or more agents from the medical device. The one or more polymers, when used to at least partially control the release of one or more agents from the medical device, can be porous or non-porous. The one or more agents can be inserted into and/or applied to one or more surface structures and/or micro-structures on the medical device, and/or be used to at least partially form one or more surface structures and/or micro-structures on the medical device. As such, the one or more agents on the medical device can be 1) coated on one or more surface regions of the medical device, 2) inserted and/or impregnated in one or more surface structures and/or micro-structures, etc., of the medical device, and/or 3) form at least a portion or be included in at least a portion of the structure of the medical device. When the one or more agents are coated on the medical device, the one or more agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more agents are optionally inserted and/or impregnated in one or more internal structures, surface structures and/or micro-structures of the medical device, 1) one or more other coating materials can be applied at least partially over the one or more internal structures, surface structures, and/or micro-structures of the medical device, and/or 2) one or more polymers can be combined with one or more agents. As such, the one or more agents can be 1) embedded in the structure of the medical device, 2) positioned in one or more internal structures of the medical device, 3) encapsulated between two polymer coatings, 4) encapsulated between the base structure and a polymer coating, 5) mixed in the base structure of the medical device that includes at least one polymer coating, or 6) one or more combinations of 1, 2, 3, 4, and/or 5. In addition or alternatively, the one or more coating of the one or more polymers on the medical device can include 1) one or more coatings of non-porous polymers, 2) one or more coatings of a combination of one or more porous polymers and one or more non-porous polymers, 3) one or more coating of porous polymer, or 4) one or more combinations of options 1, 2, and 3.

In another and/or alternative aspect of the present disclosure, different agents can optionally be located in and/or between different polymer coating layers and/or on the structure of the medical device. As can also be appreciated, many other and/or additional coating combinations and/or configurations can be used. The concentration of one or more agents, the type of polymer, the type and/or shape of internal structures in the medical device, and/or the coating thickness of one or more agents can be used to control the release time, the release rate, and/or the dosage amount of one or more agents; however, other or additional combinations can be used. As such, the agent and polymer system combination and location on the medical device can be numerous. As can also be appreciated, one or more agents can be deposited on the top surface of the medical device to provide an initial uncontrolled burst effect of the one or more agents prior to the 1) controlled release of the one or more agents through one or more layers of a polymer system that include one or more non-porous polymers, and/or 2) uncontrolled release of the one or more agents through one or more layers of a polymer system. The one or more agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition.

In another and/or alternative aspect of the present disclosure, a variety of polymers can optionally be coated on the medical device and/or be used to form at least a portion of the medical device. The one or more polymers can be used on the medical device for a variety of reasons such as, but not limited to, 1) forming a portion of the medical device, 2) improving a physical property of the medical device (e.g., improve strength, improve durability, improve biocompatibility, reduce friction, etc.), 3) forming a protective coating on one or more surface structures on the medical device, 4) at least partially forming one or more surface structures on the medical device, and/or 5) at least partially controlling a release rate of one or more agents from the medical device. As can be appreciated, the one or more polymers can have other or additional uses on the medical device. The one or more polymers can be porous, non-porous, biostable, biodegradable (i.e., dissolves, degrades, is absorbed, or any combination thereof in the body), and/or biocompatible. When the medical device is coated with one or more polymers, the polymer can include 1) one or more coatings of non-porous polymers, 2) one or more coatings of a combination of one or more porous polymers and one or more non-porous polymers, 3) one or more coatings of one or more porous polymers and one or more coatings of one or more non-porous polymers, 4) one or more coating of porous polymer, or 5) one or more combinations of options 1, 2, 3, and 4. The thickness of one or more of the polymer layers can be the same or different. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing, and/or the like; however, other or additional coating techniques can be used. The one or more polymers that can be coated on the medical device and/or used to at least partially form the medical device can be polymers that are considered to be biodegradable, bioresorbable, or bioerodable; polymers that are considered to be biostable; and/or polymers that can be made to be biodegradable and/or bioresorbable with modification. The thickness of each polymer layer is generally at least about 0.01 μm and is generally less than about 150 μm (e.g., 0.01 μm to 150 μm and all values and ranges therebetween); however, other thicknesses can be used. In one non-limiting embodiment, the thickness of a polymer layer and/or layer of agent is about 0.02-75p m, more particularly about 0.05-50 μm, and even more particularly about 1-30 μm. As can be appreciated, other thicknesses can be used.

In accordance with another and/or alternative aspect of the present disclosure, the medical device, when including and/or is coated with one or more agents, can include and/or can be coated with one or more agents that are the same or different in different regions of the medical device and/or have differing amounts and/or concentrations in differing regions of the medical device. For instance, the medical device can 1) be coated with and/or include one or more biologicals on at least one portion of the medical device and at least another portion of the medical device is not coated with and/or includes agent; 2) be coated with and/or include one or more biologicals on at least one portion of the medical device that is different from one or more biologicals on at least another portion of the medical device; and/or 3) be coated with and/or include one or more biologicals at a concentration on at least one portion of the medical device that is different from the concentration of one or more biologicals on at least another portion of the medical device.

In accordance with another and/or alternative aspect of the present disclosure, one or more portions of the medical device can optionally 1) include the same or different agents, 2) include the same or different amount of one or more agents, 3) include the same or different polymer coatings, 4) include the same or different coating thicknesses of one or more polymer coatings, 5) have one or more portions of the medical device controllably release and/or uncontrollably release one or more agents, and/or 6) have one or more portions of the medical device controllably release one or more agents and one or more portions of the medical device uncontrollably release one or more agents.

In accordance with another and/or alternative aspect of the present disclosure, one or more surfaces of the medical device can optionally be treated to achieve the desired coating properties of the one or more agents and one or more polymers coated on the medical device. Such surface treatment techniques include, but are not limited to, cleaning, buffing, smoothing, nitriding, annealing, swaging, cold working, etching (chemical etching, plasma etching, etc.), etc. As can be appreciated, other or additional surface treatment processes can be used prior to the coating of one or more agents and/or polymers on the surface of the medical device.

In another and/or alternative non-limiting aspect of the disclosure, the medical device can optionally include a marker material that facilitates enabling the medical device to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.). The marker material can form all or a portion of the medical device and/or be coated on one or more portions (flaring portion and/or body portion, at ends of medical device, at or near transition of body portion and flaring section, etc.) of the medical device. The location of the marker material can be on one or multiple locations on the medical device. The size of the one or more regions including the marker material can be the same or different. The marker material can be spaced at defined distances from one another to form ruler-like markings on the medical device to facilitate in the positioning of the medical device in a body passageway. The marker material can be a rigid or flexible material. The marker material can be a biostable or biodegradable material.

In accordance with another and/or alternative aspect of the present disclosure, the medical device or one or more regions of the medical device can optionally be constructed by use of one or more microelectromechanical manufacturing (MEMS) techniques (e.g., micro-machining, laser micro-machining, micro-molding, etc.); however, other or additional manufacturing techniques can be used.

In accordance with another and/or alternative aspect of the present disclosure, the medical device can optionally include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

In accordance with another and/or alternative aspect of the present disclosure, the medical device can optionally include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. As defined herein, a "micro-structure" is a structure having at least one dimension (e.g., average width, average diameter, average height, average length, average depth, etc.) that is no more than about 2 mm, and typically no more than about 1 mm. As can be appreciated, when the medical device includes one or more surface structures, 1) all the surface structures can be micro-structures, 2) all the surface structures can be non-micro-structures, or 3) a portion of the surface structures can be micro-structures and a portion can be non-micro-structures. Typically, the micro-structures (when formed) extend from or into the outer surface no more than about 400 microns (0.01-400 microns and all values and ranges therebetween), and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has been positioned on and/or in a patient; however, this is not required. The one or more surface structures and/or micro-structures can be used to facilitate in forming and maintaining a shape of a medical device. In one non-limiting embodiment, the one or more surface structures and/or micro-structures can be at least partially formed of an agent and/or be formed of a polymer. One or more of the surface structures and/or micro-structures can include one or more internal passageways that can include one or more materials (e.g., agent, polymer, etc.); however, this is not required. The one or more coatings and/or one or more surface structures and/or micro-structures of the medical device can be used for a variety of purposes such as, but not limited to, 1) increasing the bonding and/or adhesion of one or more agents, adhesives, marker materials, and/or polymers to the medical device, 2) changing the appearance or surface characteristics of the medical device, and/or 3) controlling the release rate of one or more agents. The one or more micro-structures and/or surface structures can be biostable, biodegradable, etc. The medical device or one or more regions of the medical device can be at least partially covered and/or filled with a protective material to at least partially protect one or more regions of the medical device, and/or one or more micro-structures, and/or surface structures on the medical device from damage. The protective material can include one or more polymers previously identified above. The protective material can be 1) biostable and/or biodegradable and/or 2) porous and/or non-porous.

In another and/or alternative aspect of the disclosure, the medical device can optionally be an expandable device that can be expanded by use of some other device (e.g., balloon, etc.). The expandable medical device can be fabricated from a material that has no or substantially no shape-memory characteristics.

In accordance with another and/or alternative aspect of the present disclosure, there is optionally provided a near net process for a frame or other metal component of the medical device. In one non-limiting embodiment of the disclosure, there is provided a method of powder pressing materials and increasing the strength post-sintering by imparting additional cold work. In one non-limiting embodiment, the green part is pressed and then sintered. Thereafter, the sintered part is again pressed to increase its mechanical strength by imparting cold work into the pressed and sintered part. Generally, the temperature during the pressing process after the sintering process is 20-100° C. (and all values and ranges therebetween), typically 20-80° C., and more typically 20-40° C. As defined herein, cold working occurs at a temperature of no more than 150° C. (e.g., 10-15%0° C. and all values and ranges therebetween). The change in the shape of the repressed post-sintered part needs to be determined so the final part (pressed, sintered and re-pressed) meets the dimensional requirements of the final formed part. There is also provided a process of increasing the mechanical strength of a pressed metal part by repressing the post-sintered part to add additional cold work into the material, thereby increasing its mechanical strength. There is also provided a process of powder pressing to a near net or final part using metal powder. In one non-limiting embodiment, there is provided a process of creating a metal part with pre-defined voids to create a trabecular or foam structure composed of mixing a metal and polymer powder, pressing the powder into a finished part or semi-finished green part, and then sintering the part under which conditions the polymer leaves the metal behind through a process of thermal degradation of the polymer. The resulting part has a porosity associated with the size of the polymer particles as well as the homogeneity of the mixture upon pressing prior to sintering. In another non-limiting embodiment, there is provided a process by which a residual of the polymer is left behind after thermal degradation, on the metal substrate, and the polymer residual has some desired biological affect (e.g., masking the metal from the body by encapsulation, promotion of cellular attachment and growth). The polymer and metal powders can be of varying sizes to create multiple voids—some large to create a pathway for cellular growth, and some small to create a ruff surface to promote cellular attachment. As can be appreciated, the polymer can be uniformly or non-uniformly dispersed with the metal powder. For example, if the final formed part is to have a uniform density and pore structure, the polymer material is uniformly dispersed with the metal powder prior to consolidating and pressing the polymer and metal powders together and then subsequently sintering together the metal powder to form the metal part or medical device. Alternatively, if the formed metal part or medical device is to have one or more channels, passageways, and/or voids on the outer surface and/or within the formed part or medical device, at least a portion of the polymer is not uniformly distributed with the metal powder, but instead is concentrated or forms all of the region that is to be the one or more channels, passageways, and/or voids on the outer surface and/or within the formed part or medical device such that when the polymer and metal powder is sintered, some or all of the polymer is degraded and removed from the part or medical device, thereby forming such one or more channels, passageways, and/or voids on the outer surface and/or within the formed part or medical device. As such, the use of the polymer in combination with metal powder and subsequent pressing and sintering can be used to form novel and customized shapes for the medical device or the near net form of the medical device. Generally, the polymer constitutes about 0.1-70 vol. % (and all values and ranges therebetween) of the consolidated and pressed material prior to the sintering step, typically the polymer constitutes about 1-60 vol. % of the consolidated and pressed material prior to the sintering step.

In accordance with another and/or alternative aspect of the present disclosure, the metal alloy used to at least partially form the medical device is initially formed into a blank, a rod, a tube, etc., and then finished into final form by one or more finishing processes. The metal alloy blank, rod, tube, etc., can be formed by various techniques such as, but not limited to, 1) melting the metal alloy and/or metals that form the metal alloy (e.g., vacuum arc melting, etc.) and then extruding and/or casting the metal alloy into a blank, rod, tube, etc., 2) melting the metal alloy and/or metals that form the metal alloy, forming a metal strip, and then rolling and welding the strip into a blank, rod, tube, etc., 3) consolidating the metal powder of the metal alloy and/or metal powder of metals that form the metal alloy into a blank, rod, tube, etc., or 4) 3-D printing the metal powder of the metal alloy and/or metal powder of metals that form the metal alloy into a blank, rod, tube, etc. When the metal alloy is formed into a blank, the shape and size of the blank is non-limiting. In one non-limiting process, the near net medical device, near net component of a medical device, blank, rod, tube, etc., can be formed from one or more ingots of metal or metal alloy. In one non-limiting process, an arc melting process (e.g., vacuum arc melting process, etc.) can be used to form the near net medical device, near net component of a medical device, blank, rod, tube, etc. In one non-limiting embodiment, the average particle size of the metal powders is less than about 230 mesh (e.g., less than 63 microns; 1-62 microns and all values and ranges therebetween). In another and/or alternative non-limiting embodiment, the average particle size of the metal powders is about 2-62 microns, and more particularly about 5-49.9 microns. In another and/or alternative non-limiting embodiment, the average particle size of the metal powders is about 10-40 microns. In another and/or alternative non-limiting embodiment, the average density of the metal powders is greater than 5 g/cm$^3$ (e.g., 5.001 g/cm$^3$ to 19.3 g/cm$^3$ and all values and ranges therebetween). In another and/or alternative non-limiting embodiment, 10-100 vol. % (and all values and ranges therebetween) of the metal powder is spherical shaped. The purity of the metal powders should be selected so that the metal powders contain very low levels of carbon, oxygen, and nitrogen. Typically, the carbon content of the metal powder used to form the metal alloy is less than about 100 ppm, the oxygen content is less than about 50 ppm, and the nitrogen content is less than about 20 ppm. Typically, metal powder used to form the metal alloy has a purity grade of at least 99.9 and more typically at least about 99.95.

In accordance with another and/or alternative aspect of the present disclosure, when the metal powder is consolidated to form the metal alloy into a blank, rod, tube, etc., the metal powder is pressed together to form a solid solution of the metal alloy into a near net medical device, near net component of a medical device, blank, rod, tube, etc. Typically, the pressing process is by an isostatic process (i.e., uniform pressure applied from all sides on the metal powder); however other processes can be used. When the metal powders are pressed together isostatically, cold isostatic pressing (CIP) is typically used to consolidate the metal powders; however, this is not required. The pressing process can be performed in an inert atmosphere, an oxygen-reducing atmosphere (e.g., hydrogen, argon and hydrogen mixture, etc.), and/or under a vacuum; however, this is not required. The average density of the near net medical device, near net component of a medical device, blank, rod, tube, etc., that is achieved by pressing together the metal powders is about 80-95% (and all values and ranges therebetween) of the final average density of the near net medical device, near net component of a medical device, blank, rod, tube, etc., or about 70-96% (and all values and ranges therebetween) the minimum theoretical density of the metal alloy. Pressing pressures of at least about 300 MPa are generally used. Generally, the pressing pressure is about 400-700 MPa; however, other pressures can be used. After the metal powders are pressed together, the pressed metal powders are sintered to partially or fully fuse the metal powders together to form the near net medical device, near net component of a medical device, blank, rod, tube, etc. The sintering of the consolidated metal powder can be performed in an oxygen-reducing atmosphere (e.g., helium, argon, hydrogen, argon and hydrogen mixture, etc.), and/or under a vacuum; however, this is not required. At the high sintering temperatures, a high hydrogen atmosphere will reduce both the amount of carbon and oxygen in the formed near net medical device, near net component of a medical device, blank, rod, tube, etc. The sintered metal powder generally has an as-sintered average density of about 90-99% the minimum theoretical density of the metal alloy.

In accordance with another and/or alternative aspect of the present disclosure, when the metal powder is used to 3D print a medical device, component of a medical device, blank, rod, tube, etc., the average particle size of the metal powder is optionally 2-62 microns, and more particularly about 5-49.9 microns, the average density of the metal powders is greater than 5 g/cm$^3$, and the metal powder is generally spherical-shaped, and the Hall flow (s/50 g) is less than 30 seconds (e.g., 2-29.99 seconds and all values and ranges therebetween).

In accordance with another and/or alternative aspect of the present disclosure, the near net medical device, near net component of a medical device, blank, rod, tube, etc., can optionally be cleaned and/or polished after the near net medical device, near net component of a medical device, blank, rod, tube, etc., has been formed; however, this is not required.

In accordance with another and/or alternative aspect of the present disclosure, the near net medical device, near net component of a medical device, blank, rod, tube, etc., can be resized to the desired dimension of the medical device. In one non-limiting embodiment, the cross-sectional area or diameter of the near net medical device, near net component of a medical device, blank, rod, tube, etc., is reduced to a final near net medical device, near net component of a medical device, blank, rod, tube, etc. dimension in a single step or by a series of steps. The reduction of the outer cross-sectional area or diameter of the near net medical device, near net component of a medical device, blank, rod, tube, etc., may be obtained by centerless grinding, turning, electropolishing, drawing process, grinding, laser cutting, shaving, polishing, EDM cutting, etc. The outer cross-sectional area or diameter size of the near net medical device, near net component of a medical device, blank, rod, tube, etc., can be reduced by the use of one or more drawing processes; however, this is not required. During the drawing process, care should be taken to not form micro-cracks in the near net medical device, near net component of a medical device, blank, rod, tube, etc., during the reduction of the near net medical device, near net component of a medical device, blank, rod, tube, etc., outer cross-sectional area or diameter.

In accordance with another and/or alternative aspect of the present disclosure, the near net medical device, near net component of a medical device, blank, rod, tube, etc., during the drawing process can optionally be nitrided; however, this is not required. The nitrided layer on the near net medical device, near net component of a medical device, blank, rod, tube, etc., can function as a lubricating surface during the drawing process to facilitate in the drawing of the near net medical device, near net component of a medical device, blank, rod, tube, etc. The near net medical device, near net component of a medical device, blank, rod, tube, etc., is generally nitrided in the presence of nitrogen or a nitrogen mixture.

The use of the metal alloy to form all or a portion of the medical device can result in several advantages over medical devices formed from other materials. These advantages include, but are not limited to:

- The metal alloy has increased strength and/or hardness compared with standard stainless steel or standard chromium-cobalt alloys or standard titanium alloys, thus a lesser quantity of metal alloy can be used in the medical device to achieve similar strengths compared to medical devices formed of different metals. As such, the resulting medical device can be made smaller and less bulky by use of the metal alloy without sacrificing the strength and durability of the medical device. The medical device can also have a smaller profile, thus can be inserted into smaller areas, openings, and/or passageways. The thinner struts of metal alloy to form the frame or other portions of the medical device can be used to form a frame or other portion of the medical device having a strength that would require thicker struts or other structures of the medical device when formed by standard stainless steel, standard chromium-cobalt alloys, or standard titanium alloys.
- The increased strength of the metal alloy also results in the increased radial strength of the medical device. For instance, the thickness of the walls of the medical device can be made thinner and achieve a similar or improved radial strength as compared with thicker-walled medical devices formed of standard stainless steel, standard cobalt and chromium alloy, or standard titanium alloy.

The metal alloy has improved stress-strain properties, bendability properties, elongation properties, and/or flexibility properties of the medical device compared with standard stainless steel or standard chromium-cobalt alloys, thus resulting in an increased life for the medical device. For instance, the medical device can be used in regions that subject the medical device to repeated bending. Due to the improved physical properties of the medical device from the metal alloy, the medical device has improved resistance to fracturing in such frequent bending environments. These improved physical properties at least in part result from the composition of the metal alloy, the grain size of the metal alloy, the carbon, oxygen, and nitrogen content of the metal alloy, and/or the carbon/oxygen ratio of the metal alloy.

The metal alloy can have a reduced degree of recoil during the crimping and/or expansion of the medical device compared with standard stainless steel or standard chromium-cobalt alloys or standard titanium alloys. The medical device formed of the metal alloy better maintains its crimped form and/or better maintains its expanded form after expansion due to the use of the metal alloy. As such, when the medical device is to be mounted onto a delivery device when the medical device is crimped, the medical device better maintains its smaller profile during the insertion of the medical device in a body passageway. Also, the medical device better maintains its expanded profile after expansion to facilitate in the success of the medical device in the treatment area.

The use of metal alloy in the medical device medical device can result in the medical device better conforming to an irregularly shaped body passageway when expanded in the body passageway as compared to a medical device formed by standard stainless steel, standard chromium-cobalt alloys, or standard titanium alloys.

The metal alloy can have improved fatigue ductility when subjected to cold-working as compared to the cold-working of standard stainless steel, standard chromium-cobalt alloys, or standard titanium alloys.

The metal alloy can have improved durability compared to standard stainless steel, standard chromium-cobalt alloys, or standard titanium alloys.

The metal alloy can have improved hydrophilicity compared to standard stainless steel, standard chromium-cobalt alloys, or standard titanium alloys.

The metal alloy can have reduced ion release in the body passageway as compared to standard stainless steel, standard chromium-cobalt alloys, or standard titanium alloys.

The metal alloy can be less of an irritant to the body than standard stainless steel, standard cobalt-chromium alloy, or standard titanium alloys, thus can result in reduced inflammation, faster healing, and increased success rates of the medical device.

The medical devices which include expandable metal frames that are at least partially formed of metal alloy can exhibit reduced amount of recoil, improved bending conformity, and greater radial strength compared to expandable frames formed of standard stainless steel, standard cobalt-chromium alloy, and standard TiAlV alloy, thereby resulting in the following non-limiting advantages compared to expandable frames formed of standard stainless steel, standard cobalt-chromium alloy, or standard TiAlV alloy: 1) the formation of a frame for a medical device having thinner posts, struts, and/or strut joints which results in i) safer vascular access when inserting the medical device through a body passageway and to the treatment area, and/or ii) decreased risk of bleeding and/or damage to the body passageway and/or the treatment area when the medical device is delivered to the treatment area and/or expanded at the treatment area; 2) easier deliverability of the medical device to the treatment area which can result in i) decreased trauma to the body passageway (e.g., blood vessel, aortic arch trauma, etc.) during the insertion and/or expansion of the medical device at the treatment area, and/or ii) decreased risk of neuro complications-stroke; 3) less recoil which results in i) reduced crimping profile size, ii) increased conformability of the expanded medical device at the treatment area after expansion in the treatment area, iii) increased radial strength of the frame of the medical device after expansion at the treatment area, iv) only require a single crimping cycle to crimp the medical device on a balloon catheter or other type of delivery device, v) reduced incidence of damage to components of the medical device (e.g., struts, posts, strut joints, and/or other components of the expandable frame, leaflets, skirts, coatings, etc.) during the crimping, expansion, and operation of the medical device, vi) greater effective orifice area (EOA) of the medical device after expansion of the medical device, vi) decreased pulmonary valve regurgitation (PVR) after expansion of the medical device in the treatment area, and/or vii) require only a single expansion cycle of the balloon on the balloon catheter or other expansion mechanism to fully expand the medical device; and/or 4) creating a medical device having superior material biologic properties to i) improve tissue adhesion and/or growth on or about medical device, ii) reduce adverse tissue reactions with the medical device, iii) reduce toxicity of medical device, iv) potentially decrease in-valve thrombosis during the life of the medical device, and/or v) reduce the incidence of infection during the life of the medical device.

Medical devices, such as expandable medical devices (e.g., expandable heart valves, stents, etc.) that include the metal alloy in accordance with the present disclosure can overcome several unmet needs that exist in expandable medical device that are formed of standard cobalt-chromium alloys, standard TiAlV alloys, and standard stainless steel, namely 1) not having to form a large hole in large arterial vessels or other blood vessels for initial insertion of the crimped medical device into the atrial vessel or other blood vessel, thereby reducing the incidence of lethal bleeding during a treatment; 2) enabling the medical device to be delivered and implanted in abnormally shaped heart valves or through an abnormally shaped arterial vessel; 3) reducing the incidence of a perivalvular leak and/or other types of leakage about the implanted medical device when the medical device is expanded; 4) improving the radial strength of the expanded struts, posts, and/or strut joints in the expandable frame and the strength of the expandable frame itself after expansion the medical device; 5) reducing the amount of recoil of the expandable frame during the crimping and/or expansion of the expandable frame of the medical device; 6) enabling the medical device to be used in a heart that has a permanent pacemaker; 7) reducing the incidence of minor stroke during the insertion and operation of the medical device at the treatment area; 8) reducing the incidence of coronary ostium compromise; 9) improving foreshortening;

10) reducing further aortic valve calcification and/or calcification in a blood vessel after implantation of the medical device; 11) reducing the need for multiple crimping cycles when inserting the medical device on a catheter or other type of delivery system; 12) reducing the incidence of frame/stent fracture during the crimping and/or expansion of the medical device; 13) reducing the incidence of biofilm-endocarditis after implantation of the medical device; 14) reducing allergic reactions to the medical device after implantation of the medical device; 15) improving the hydrophilicity of the medical device to improve tissue growth on and/or about the implanted medical device, 16) reducing the magnetic susceptibility of the medical device, 17) reducing the toxicity of the medical device, 18) reducing the amount of metal ion release from the medical device, and/or 19) increasing the longevity of leaflets and/or stent/frame and/or other components of the medical device after insertion of the medical device.

One non-limiting object of the present disclosure is the provision of metal alloy in accordance with the present disclosure that exhibits a rhenium effect and that can optionally be used to partially or fully form a medical device.

Another and/or alternative non-limiting object of the present disclosure is the provision of metal alloy in accordance with the present disclosure that exhibits a rhenium effect and includes at least 15 awt. % rhenium.

Another and/or alternative non-limiting object of the present disclosure is the provision of a method and process for forming the metal alloy in accordance with the present disclosure that exhibits a rhenium effect and that inhibits or prevents the formation of micro-cracks during the processing of the metal alloy.

Another and/or alternative non-limiting object of the present disclosure is the provision of a medical device that is partially or fully formed of the metal alloy in accordance with the present disclosure that exhibits a rhenium effect and wherein the medical device has improved physical properties.

Another and/or alternative non-limiting object of the present disclosure is the provision of a medical device that is at least partially formed of the metal alloy in accordance with the present disclosure that exhibits a rhenium effect wherein the medical device has increased strength and/or hardness.

Another and/or alternative non-limiting object of the present disclosure is the provision of a method and process for forming the metal alloy in accordance with the present disclosure that exhibits a rhenium effect and that inhibits or prevents crack propagation and/or fatigue failure of the metal alloy.

Another and/or alternative non-limiting object of the present disclosure is the provision of a metal alloy that exhibits a rhenium effect and wherein the metal alloy comprises rhenium, molybdenum, and one or more additional additives.

Another and/or alternative non-limiting object of the present disclosure is the provision of a metal alloy that exhibits a rhenium effect and wherein the metal alloy comprises rhenium, molybdenum, chromium, and optionally and one or more additional additives.

Another and/or alternative non-limiting object of the present disclosure is the provision of a medical device that includes a metal alloy that exhibits a rhenium effect and wherein the metal alloy comprises rhenium, molybdenum, and one or more additional additives; and wherein the medical device optionally includes an expandable frame.

Another and/or alternative non-limiting object of the present disclosure is the provision of a medical device that includes a metal alloy that exhibits a rhenium effect and wherein the metal alloy comprises rhenium, molybdenum, chromium, and optionally one or more additional additives; and wherein the medical device optionally includes an expandable frame.

Another and/or alternative non-limiting object of the present disclosure is the provision of a medical device that includes a metal alloy that exhibits a rhenium effect and wherein the metal alloy comprises rhenium, molybdenum, and one or more additional additives; and wherein the medical device optionally includes an expandable frame; and wherein the expandable frame includes a plurality of struts.

Another and/or alternative non-limiting object of the present disclosure is the provision of a medical device that includes a metal alloy that exhibits a rhenium effect and wherein the metal alloy comprises rhenium, molybdenum, chromium, and optionally one or more additional additives; and wherein the medical device optionally includes an expandable frame; wherein the expandable frame includes a plurality of struts.

Another and/or alternative non-limiting object of the present disclosure is the provision of a medical device that includes a metal alloy wherein that exhibits a rhenium effect and the metal alloy comprises rhenium, molybdenum, and one or more alloying metals; and wherein the medical device includes an expandable frame; wherein the expandable frame is configured to be crimped to a crimped state such that a maximum outer diameter of the expandable frame when in the crimped state is less than a maximum outer diameter of the expandable frame when fully expanded to an expanded state.

Another and/or alternative non-limiting object of the present disclosure is the provision of a medical device that includes a metal alloy wherein that exhibits a rhenium effect and the metal alloy comprises rhenium, molybdenum, chromium, and optionally one or more alloying metals; and wherein the medical device includes an expandable frame; wherein the expandable frame is configured to be crimped to a crimped state such that a maximum outer diameter of the expandable frame when in the crimped state is less than a maximum outer diameter of the expandable frame when fully expanded to an expanded state.

Another and/or alternative non-limiting object of the present disclosure is the provision of a medical device that includes a metal alloy that exhibits a rhenium effect and wherein the metal alloy comprises rhenium, molybdenum, and one or more alloying metals; and wherein the medical device includes an expandable frame; wherein the expandable frame has a recoil of less than 5% after being subjected to a first crimping process.

Another and/or alternative non-limiting object of the present disclosure is the provision of a medical device that includes a metal alloy that exhibits a rhenium effect and wherein the metal alloy comprises rhenium, molybdenum, chromium, and optionally one or more alloying metals; and wherein the medical device includes an expandable frame; wherein the expandable frame has a recoil of less than 5% after being subjected to a first crimping process.

Another and/or alternative non-limiting object of the present disclosure is the provision of a medical device that includes a metal alloy that exhibits a rhenium effect and wherein the metal alloy comprises rhenium, molybdenum, and one or more alloying metals; and wherein the medical device includes an expandable frame; wherein the expandable frame has a recoil of less than 5% after being expanded from the crimped state to the expanded state.

Another and/or alternative non-limiting object of the present disclosure is the provision of a medical device that includes a metal alloy that exhibits a rhenium effect and wherein the metal alloy comprises rhenium, molybdenum, chromium and optionally one or more alloying metals; and wherein the medical device includes an expandable frame; wherein the expandable frame has a recoil of less than 5% after being expanded from the crimped state to the expanded state.

Another and/or alternative non-limiting object of the present disclosure is the provision of a medical device that includes a metal alloy that exhibits a rhenium effect and wherein the metal alloy comprises rhenium, molybdenum, and one or more alloying metals; and wherein the metal alloy has a hydrophilicity wherein a contact angle of a water droplet on a surface of the metal alloy of 25-45° (and all values and ranges therebetween).

Another and/or alternative non-limiting object of the present disclosure is the provision of a medical device that includes a metal alloy that exhibits a rhenium effect and wherein the metal alloy comprises rhenium, molybdenum, and one or more alloying metals; and wherein the metal alloy has a maximum ion release of a primary component of the metal alloy when inserted or implanted on or in the body of the patient of no more than 0.5 $\mu g/cm^2$ per day; and wherein a primary component of the rhenium alloy is a metal in the rhenium alloy that constitutes at least 2 wt. % of the metal alloy.

Another and/or alternative non-limiting object of the present disclosure is the provision of a medical device that includes a metal alloy that exhibits a rhenium effect and wherein the metal alloy comprises rhenium, molybdenum, and one or more alloying metals; and wherein the metal alloy has an absolute increase in ion release per dose of the metal alloy in tissue about the medical device of no more than 50 days after inserted or implanted on or in the body of a patient.

Another and/or alternative non-limiting object of the present disclosure is the provision of a medical device that includes a metal alloy that exhibits a rhenium effect and wherein the medical device is an expandable stent or an expandable prosthetic heart valve.

Another and/or alternative non-limiting object of the present disclosure is the provision of a medical device that can be formed by one or more manufacturing processes. These manufacturing processes can include, but are not limited to, laser cutting, etching, annealing, drawing, pilgering, electroplating, electro-polishing, machining, plasma coating, 3D printed coatings, 3D printing, chemical vapor deposition, chemical polishing, cleaning, pickling, ion beam deposition or implantation, sputter coating, vacuum deposition, etc. In one non-limiting embodiment, at least a portion or all of the medical device is formed by a 3D printing process.

Another and/or alternative non-limiting object of the present disclosure is the provision of a metal alloy that includes a unique combination of the metals that exhibits a "rhenium effect" and results in 1) a medical device having the desired high ductility at about room temperature, 2) a medical device having the desired amount of tensile elongation, 3) a homogeneous or solid solution of a metal alloy having high radiopacity, 4) a reduction or prevention of micro-crack formation and/or breaking of the metal alloy of the present disclosure tube when the tube is sized and/or cut to form the medical device or portion of the medical device (e.g., frame of the medical device, etc.), 5) a reduction or prevention of micro-crack formation and/or breaking of the medical device or portion of the medical device (e.g., frame of the medical device, etc.) when the medical device or portion of the medical device (e.g., frame of the medical device, etc.) is crimped, 6) a reduction or prevention of micro-crack formation and/or breaking of the medical device or portion of the medical device (e.g., frame of the medical device, etc.) when the medical device is bent and/or expanded in a body passageway, 7) a medical device having the desired ultimate tensile strength and yield strength, 8) a medical device or portion of the medical device (e.g., frame of the medical device, etc.) having very thin wall thicknesses and still having the desired radial forces needed to retain the medical device or portion of the medical device (e.g., frame of the medical device, etc.) on an open state when expanded, 9) a medical device or portion of the medical device (e.g., frame of the medical device, etc.) exhibiting less recoil when the medical device or portion of the medical device (e.g., frame of the medical device, etc.) is crimped onto a delivery system and/or expanded in a body passageway, 10) a medical device exhibiting improved conformity to the shape of the treatment area in the body passageway when the medical device is expanded in a body passageway, 11) a medical device exhibiting improved fatigue ductility, 12) a medical device exhibiting reduced foreshortening when expanded, and/or 13) a medical device that exhibits improved durability.

Another and/or alternative non-limiting object of the present disclosure is the provision of a metal alloy wherein the average grain size of the metal alloy that exhibits a rhenium effect and can be about 4-20 ASTM, the tensile elongation of the metal alloy can be about 25-50%, the average density of the metal alloy can be at least about 5 gm/cc, the average yield strength of the metal alloy can be about 70-250 (ksi), the average ultimate tensile strength of the metal alloy can be about 80-550 UTS (ksi), and an average Vickers hardness can be 234 DPH to 700 DPH or a Rockwell C hardness of 19-60 at 77° F.; however, this is not required.

Another and/or alternative non-limiting object of the present disclosure is the provision of a metal alloy that includes rhenium in an amount of at least 15 awt. % of the metal alloy; and wherein the metal alloy includes one or more alloying metals selected from the group consisting of aluminum, bismuth, chromium, cobalt, copper, hafnium, iridium, iron, magnesium, manganese, molybdenum, nickel, niobium, osmium, platinum, rhodium, ruthenium, silicon, silver, tantalum, technetium, tin, titanium, tungsten, vanadium, yttrium, and zirconium; and wherein the metal alloy has a) an increase of at least 10% in ductility as compared to said metal alloy that is absent rhenium, and/or b) an increase of at least 10% in tensile strength.

Another and/or alternative non-limiting object of the present disclosure is the provision of a metal alloy that includes rhenium in an amount of at least 15 awt. % of the metal alloy and less than 50 wt. % rhenium; and wherein the metal alloy includes one or more alloying metals selected from the group consisting of aluminum, bismuth, chromium, cobalt, copper, hafnium, iridium, iron, magnesium, manganese, molybdenum, nickel, niobium, osmium, platinum, rhodium, ruthenium, silicon, silver, tantalum, technetium, tin, titanium, tungsten, vanadium, yttrium, and zirconium; and wherein the metal alloy has a) an increase of at least 10% in ductility as compared to said metal alloy that is absent rhenium, and/or b) an increase of at least 10% in tensile strength.

Another and/or alternative non-limiting object of the present disclosure is the provision of a metal alloy that comprises at least 15 awt. % rhenium and 50-78 wt. % iron (and all values and ranges therebetween), and one or more of a) 9-27 wt. % chromium (and all values and ranges therebetween), b) 0.1-26 wt. % nickel (and all values and ranges therebetween), c) 0.01-7 wt. % molybdenum (and all values and ranges therebetween), d) 0.01-16 wt. % manganese (and all values and ranges therebetween), e) 0.01-4 wt. % silicon (and all values and ranges therebetween), f) 0.01-2 wt. % titanium (and all values and ranges therebetween), g) 0.01-1 wt. % selenium (and all values and ranges therebetween), h) 0.01-1 wt. % niobium (and all values and ranges therebetween), i) 0.01-2 wt. % aluminum (and all values and ranges therebetween), j) 0.01-1 wt. % tantalum (and all values and ranges therebetween), k) 0.01-1 wt. % cobalt (and all values and ranges therebetween), l) 0.01-5 wt. % copper (and all values and ranges therebetween), m) 0.01-1 wt. % vanadium (and all values and ranges therebetween), and n) 0.01-2 wt. % tungsten (and all values and ranges therebetween).

Another and/or alternative non-limiting object of the present disclosure is the provision of a metal alloy that comprises at least 15 awt. % rhenium and 35-68 wt. % cobalt (and all values and ranges therebetween), and one or more of a) 12-28 wt. % chromium (and all values and ranges therebetween), b) 0.01-38 wt. % nickel (and all values and ranges therebetween), c) 0.1-30 wt. % molybdenum (and all values and ranges therebetween), d) 0.01-2 wt. % manganese (and all values and ranges therebetween), e) 0.01-1 wt. % silicon (and all values and ranges therebetween), f) 0.01-18 wt. % tungsten (and all values and ranges therebetween), g) 0.01-0.5 wt. % lanthanum (and all values and ranges therebetween), h) 0.01-20% wt. % iron (and all values and ranges therebetween), i) 0.01-5 wt. % titanium (and all values and ranges therebetween), j) 0.01-2 wt. % niobium (and all values and ranges therebetween), k) 0.01-2 wt. % aluminum (and all values and ranges therebetween), l) 0.01-1 wt. % silicon (and all values and ranges therebetween), m) 0.01-0.5 wt. % boron (and all values and ranges therebetween), and n) 0.01-0.5 wt. % silver (and all values and ranges therebetween).

Another and/or alternative non-limiting object of the present disclosure is the provision of a metal alloy that comprises at least 15 awt. % rhenium and 70-91.5 wt. % titanium (and all values and ranges therebetween), and one or more of a) 2-8 wt. % aluminum (and all values and ranges therebetween), b) 0.01-16 wt. % vanadium (and all values and ranges therebetween), c) 0.01-1 wt. % iron (and all values and ranges therebetween), d) 0.01-0.5 wt. % yttrium (and all values and ranges therebetween), e) 0.01-20% wt. % chromium (and all values and ranges therebetween), f) 0.0-16 wt. % molybdenum (and all values and ranges therebetween), g) 0.01-2 wt. % nickel (and all values and ranges therebetween), h) 0.01-12% wt. % tin (and all values and ranges therebetween), i) 0.01-6 wt. % zirconium (and all values and ranges therebetween), j) 0.01-2 wt. % tantalum (and all values and ranges therebetween), k) 0.01-4 wt. % niobium (and all values and ranges therebetween), l) 0.01-1 wt. % silicon (and all values and ranges therebetween), m) 0.01-3 wt. % iron (and all values and ranges therebetween).

Another and/or alternative non-limiting object of the present disclosure is the provision of a metal alloy that comprises at least 15 awt. % rhenium, 35-84 wt. % tantalum (and all values and ranges therebetween), and one or more of a) 0.1-25 wt. % tungsten (and all values and ranges therebetween), b) 0.1-55 wt. % molybdenum (and all values and ranges therebetween), c) 0.01-45 wt. % niobium (and all values and ranges therebetween), d) 0.01-5 wt. % chromium (and all values and ranges therebetween), f) 0.01-5 wt. % titanium (and all values and ranges therebetween), g) 0.01-5 wt. % zirconium (and all values and ranges therebetween), and h) 0.01-4 wt. % hafnium (and all values and ranges therebetween).

Another and/or alternative non-limiting object of the present disclosure is the provision of a metal alloy that comprises at least 15 awt. % rhenium, 40-93 wt. % molybdenum (and all values and ranges therebetween), and one or more of a) 0.1-50 wt. % tantalum (and all values and ranges therebetween), b) 0.1-50 wt. % tungsten (and all values and ranges therebetween), c) 0.01-5 wt. % hafnium (and all values and ranges therebetween), d) 0.01-20% wt. % chromium (and all values and ranges therebetween), e) 0.01-3 wt. % titanium (and all values and ranges therebetween), and f) 0.01-2 wt. % zirconium (and all values and ranges therebetween).

Another and/or alternative non-limiting object of the present disclosure is the provision of a metal alloy that comprises at least 15 awt. % rhenium, 40-85 wt. % tungsten (and all values and ranges therebetween), and one or more of a) 0.01-50 wt. % molybdenum (and all values and ranges therebetween), b) 0.01-50 wt. % tantalum (and all values and ranges therebetween), d) 0.01-5 wt. % hafnium (and all values and ranges therebetween), d) 0.01-50 wt. % copper (and all values and ranges therebetween), e) 0.01-8 wt. % nickel (and all values and ranges therebetween), f) 0.01-5 wt. % iron (and all values and ranges therebetween), g) 0.01-50 wt. % zirconium (and all values and ranges therebetween), and h) 0.01-20% wt. % chromium (and all values and ranges therebetween).

Another and/or alternative non-limiting object of the present disclosure is the provision of a metal alloy that comprises at least 15 awt. % rhenium, 40-85 wt. % niobium (and all values and ranges therebetween), and one or more of a) 0.01-20% wt. % molybdenum (and all values and ranges therebetween), b) 0.01-35 wt. % tantalum (and all values and ranges therebetween), c) 0.01-12% wt. % hafnium (and all values and ranges therebetween), d) 0.01-5 wt. % zirconium (and all values and ranges therebetween), e) 0.01-3 wt. % titanium (and all values and ranges therebetween), f) 0.01-15 wt. % tungsten (and all values and ranges therebetween), and g) 0.01-1 wt. % yttrium (and all values and ranges therebetween).

Another and/or alternative non-limiting object of the present disclosure is the provision of a metal alloy that comprises at least 15 awt. % rhenium, 30-58 wt. % titanium (and all values and ranges therebetween), and 30-58 wt. % nickel (and all values and ranges therebetween).

Another and/or alternative non-limiting object of the present disclosure is the provision of a metal alloy that comprises at least 15 awt. % rhenium, and one or more of a) 1-85 awt. % chromium (and all values and ranges therebetween), b) 0.1-10% awt. % titanium (and all values and ranges therebetween), c) 0.1-10% awt. % molybdenum (and all values and ranges therebetween), and d) 0.1-10% awt. % zirconium (and all values and ranges therebetween).

Other objects, advantages, and novel features of the present invention will become apparent from the following detailed description of the invention when considered in conjunction with the accompanying drawings.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION OF NON-LIMITING EMBODIMENTS

Figure 1:
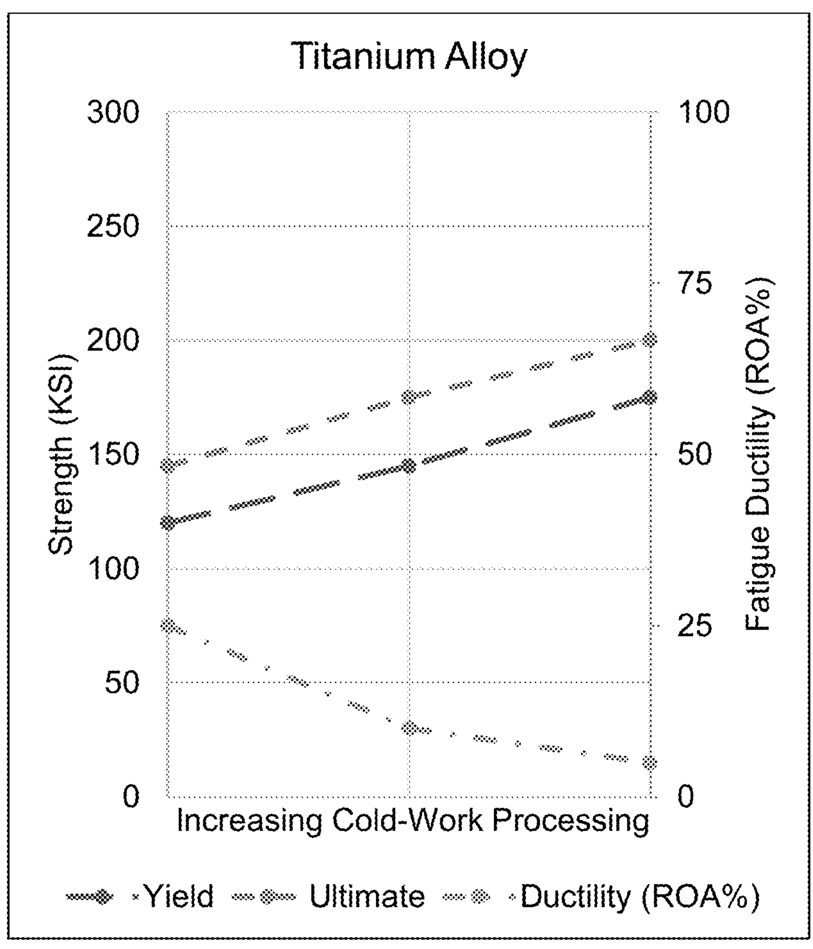
FIGS. 1-3 provide a comparison of the tensile strength, the yield strength and the ductility of a titanium alloy, a cobalt-chromium alloy and a molybdenum-rhenium alloy.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Figure 2:
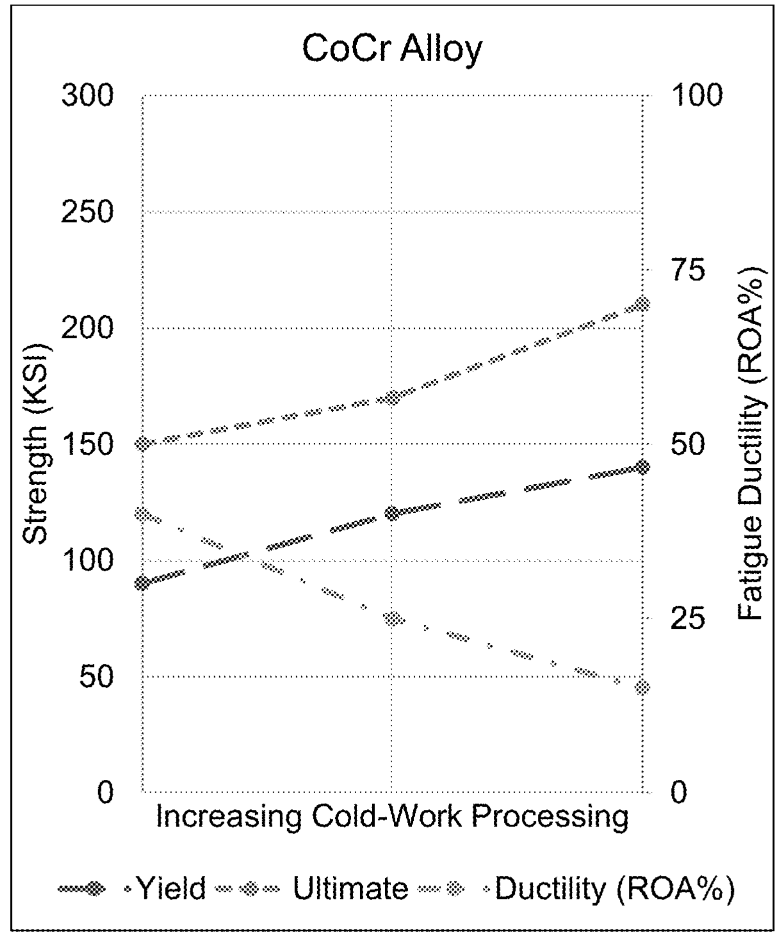
Figure 3:
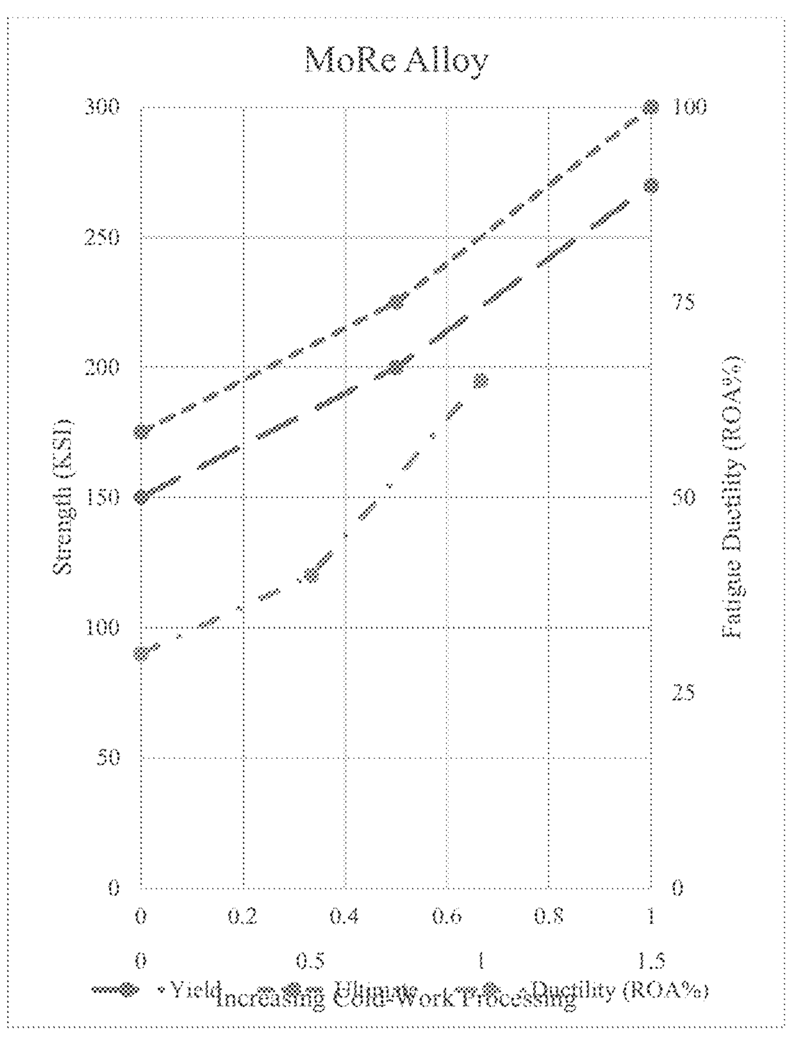

Referring now to FIGS. 1-3, there is illustrated a comparison of the tensile strength, the yield strength, and the ductility of a titanium alloy, a cobalt-chromium alloy, and a molybdenum-rhenium alloy. The titanium alloy is a Ti-6Al-4V alloy. The cobalt-chromium alloy is a MP35N alloy. The molybdenum-rhenium alloy is a 50 wt. % molybdenum and 50 wt. % rhenium alloy. As illustrated in the FIGS. 1-3, as the titanium alloy and cobalt-chromium alloy are cold worked and the cross-sectional area is reduced, the ductility of the two metal alloys reduces. However, as the molybdenum-rhenium alloy is cold worked and the cross-sectional area is reduced, the ductility of the molybdenum-rhenium increases. This increase in ductility was observed in other metal alloys that included rhenium. This increase in ductility of a cold worked metal alloys is referred to as the rhenium effect. When sufficient quantities of rhenium are included in a metal alloy, it was found that the ductility of the metal alloy with the rhenium addition either a) reduced at a significantly less rate as compared to the metal alloy that was absent sufficient amounts of rhenium, or b) increase in ductility as compared to a reduction in ductility as compared to the metal alloy that was absent sufficient amounts of rhenium. The rhenium effect was observed in several metal alloys once the atomic weight of the rhenium in the metal alloy was at least 15%.

FIGS. 1-3 also illustrate that the percentage yield and tensile strength increases in the molybdenum-rhenium alloy that has been cold worked and the cross-sectional area has been reduced is greater than the percentage yield and tensile strength increases of the titanium alloy and the cobalt-chromium alloy that has been similarly cold worked and has the cross-sectional area reduced. After the molybdenum-rhenium alloy had been cold worked and the cross-sectional area had been reduced by 50%, the yield tensile strength increased by about 33% (150 ksi to 200 ksi) and the yield strength increased about 29% (175 ksi to 225 ksi). After the molybdenum-rhenium alloy had been cold worked and the cross-sectional area had been reduced by 100%, the yield tensile strength increased by about 73% (150 ksi to 260 ksi) and the yield strength increased about 71% (175 ksi to 300 ksi). The percentage increase in tensile strength of the molybdenum-rhenium is greater than the percentage increase in tensile strength of the titanium alloy and the cobalt-chromium alloy that has been similarly cold worked and has the cross-sectional area reduced.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall therebetween.

To aid the Patent Office and any readers of this application and any resulting patent in interpreting the claims appended hereto, applicants do not intend any of the appended claims or claim elements to invoke 35 U.S.C. 112(f) unless the words "means for" or "step for" are explicitly used in the particular claim.

What is claimed:

1. A medical device that is at least partially formed of said metal alloy; said metal alloy includes rhenium and iron; said metal alloy includes at least 15 awt. % rhenium and 50-78 wt. % iron, and one or more of a) 9-27 wt. % chromium, b) 0.1-26 wt. % nickel, c) 0.01-7 wt. % molybdenum, d) 0.01-16 wt. % manganese, e) 0.01-4 wt. % silicon, f) 0.01-2 wt. % titanium, g) 0.01-1 wt. % selenium, h) 0.01-1 wt. % niobium, i) 0.01-2 wt. % aluminum, j) 0.01-1 wt. % tantalum, k) 0.01-1 wt. % cobalt, l) 0.01-5 wt. % copper, m) 0.01-1 wt. % vanadium, and n) 0.01-2 wt. % tungsten.

2. The medical device as defined in claim 1, wherein said metal alloy includes less than 35 wt. % rhenium.

3. The medical device as defined in claim 1, wherein said metal alloy includes less than 25 wt. % rhenium.

4. The medical device as defined in claim 1, wherein said metal alloy has a) an increase of at least 10% in ductility as compared to said metal alloy that is absent rhenium, and/or b) an increase of at least 10% in tensile strength as compared to said metal alloy that is absent rhenium.

5. The medical device as defined in claim 1, wherein said medical device is selected from the group consisting of a stent, a valve, spinal implant, bone implant, dental implant, bone plate, screw, rod, and post.

6. The medical device as defined in claim 5, wherein said medical device includes an expandable frame formed of said metal alloy; said expandable frame includes a plurality of struts; said expandable frame is configured to be crimped to a crimped state such that a maximum outer diameter of said expandable frame when in said crimped state is less than a maximum outer diameter of said expandable frame when fully expanded to an expanded state; said expandable frame includes one or more properties selected from the group consisting of a) said expandable frame has a recoil of less than 5% after being subjected to a first crimping process; b) said expandable frame has a recoil of less than 5% after being expanded from said crimped state to said expanded state; c) said expandable frame that is formed of said metal alloy has a hydrophilicity wherein a contact angle of a water droplet on a surface of said metal alloy is 25-45°; d) said metal alloy that at least partially forms said expandable frame has a maximum ion release of a primary component of said metal alloy when inserted or implanted on or in the body of the patient of no more than 0.5 μg/cm$^2$ per day, wherein said primary component constitutes at least 2 wt. % of said metal alloy; and/or e) said metal alloy that at least partially forms said expandable frame has an absolute increase in ion release per dose of metal alloy in tissue about said medical device of no more than 50 days after inserted or implanted on or in the body of a patient.

7. A medical device that is at least partially formed of said metal alloy; said metal alloy includes rhenium and iron; said metal alloy includes at least 15 awt. % rhenium and at least 50 wt. % iron, and one or more a) 10-28 wt. % chromium, b) 0-35 wt. % nickel, c) 0-4 wt. % molybdenum, d) 0-2 wt. % manganese, e) 0-0.75 wt. % silicon, f) 0-0.3 wt. % carbon, g) 0-5 wt. % titanium, h) 0-10 wt. % niobium, i) 0-5 wt. % copper, j) 0-4 wt. % aluminum, k) 0-10 wt. % tantalum, k) 0-1 wt. % selenium, m) 0-2 wt. % vanadium, and/or n) 0-2 wt. % tungsten.

8. The medical device as defined in claim 7, wherein said metal alloy includes less than 35 wt. % rhenium.

9. The medical device as defined in claim 7, wherein said metal alloy includes less than 25 wt. % rhenium.

10. The medical device as defined in claim 7, wherein said metal alloy has a) an increase of at least 10% in ductility as compared to said metal alloy that is absent rhenium, and/or b) an increase of at least 10% in tensile strength as compared to said metal alloy that is absent rhenium.

11. The medical device as defined in claim 7, wherein said medical device is selected from the group consisting of a stent, a valve, spinal implant, bone implant, dental implant, bone plate, screw, rod, and post.

12. The medical device as defined in claim 11, wherein said medical device includes an expandable frame formed of said metal alloy; said expandable frame includes a plurality of struts; said expandable frame is configured to be crimped to a crimped state such that a maximum outer diameter of said expandable frame when in said crimped state is less than a maximum outer diameter of said expandable frame when fully expanded to an expanded state; said expandable frame includes one or more properties selected from the group consisting of a) said expandable frame has a recoil of less than 5% after being subjected to a first crimping process; b) said expandable frame has a recoil of less than 5% after being expanded from said crimped state to said expanded state; c) said expandable frame that is formed of said metal alloy has a hydrophilicity wherein a contact angle of a water droplet on a surface of said metal alloy is 25-45°; d) said metal alloy that at least partially forms said expandable frame has a maximum ion release of a primary component of said metal alloy when inserted or implanted on or in the body of the patient of no more than 0.5 μg/cm$^2$ per day, wherein said primary component constitutes at least 2 wt. % of said metal alloy; and/or e) said metal alloy that at least partially forms said expandable frame has an absolute increase in ion release per dose of metal alloy in tissue about said medical device of no more than 50 days after inserted or implanted on or in the body of a patient.

* * * * *